(12) United States Patent
Gottschall et al.

(10) Patent No.: US 9,061,267 B2
(45) Date of Patent: Jun. 23, 2015

(54) SPECIFIC SORBENT FOR BINDING PROTEINS AND PEPTIDES, AND SEPARATION METHOD USING THE SAME

(75) Inventors: Klaus Gottschall, Heddesheim (DE); Markus Arendt, Hockenheim (DE); Andres Kirschfeld, Hirschberg (DE); Christian Meyer, Ludwigshafen (DE); Markus Weis, Ludwigshafen (DE); Martin Welter, Heidelberg (DE); Lothar Ziser, Altrip (DE)

(73) Assignee: INSTRACTION GMBH, Mannheim (DE)

( * ) Notice: Subject to any disclaimer, the term of this patent is extended or adjusted under 35 U.S.C. 154(b) by 368 days.

(21) Appl. No.: 13/515,653

(22) PCT Filed: Dec. 17, 2010

(86) PCT No.: PCT/EP2010/007759
§ 371 (c)(1),
(2), (4) Date: Sep. 19, 2013

(87) PCT Pub. No.: WO2011/072873
PCT Pub. Date: Jun. 23, 2011

(65) Prior Publication Data
US 2014/0005364 A1    Jan. 2, 2014

(30) Foreign Application Priority Data
Dec. 17, 2009   (EP) ..................... 09015647

(51) Int. Cl.
*B01J 20/26*    (2006.01)
*B01J 43/00*    (2006.01)
*C07K 1/18*    (2006.01)
*B01D 15/38*    (2006.01)
*B01J 20/32*    (2006.01)
*C07K 1/22*    (2006.01)
*C07K 16/06*    (2006.01)

(52) U.S. Cl.
CPC ............... *B01J 20/267* (2013.01); *B01J 43/00* (2013.01); *C07K 1/18* (2013.01); *B01D 15/3804* (2013.01); *B01J 20/265* (2013.01); *B01J 20/3242* (2013.01); *B01J 20/3246* (2013.01); *B01J 20/3248* (2013.01); *B01J 20/3255* (2013.01); *B01J 20/3282* (2013.01); *B01J 20/3285* (2013.01); *C07K 1/22* (2013.01); *C07K 16/065* (2013.01)

(58) Field of Classification Search
None
See application file for complete search history.

(56) References Cited

U.S. PATENT DOCUMENTS

| 7,008,542 B2 * | 3/2006 | Belew et al. .................. 210/660 |
| 2011/0086935 A1 | 4/2011 | Schelhaas et al. |
| 2011/0180407 A1 * | 7/2011 | Tyrrell et al. .................. 204/450 |

FOREIGN PATENT DOCUMENTS

| DE | 10 2008 012224 | 9/2009 |
| EP | 1715039 | 10/2006 |
| WO | WO98/08603 | 3/1998 |
| WO | WO00/69872 | 11/2000 |

OTHER PUBLICATIONS

International Search Report for PCT/EP2010/007759 of Feb. 11, 2011.

* cited by examiner

Primary Examiner — Jeffrey E Russel
(74) Attorney, Agent, or Firm — Hueschen and Sage

(57) ABSTRACT

Sorbent comprising a solid support material, the surface of which comprises a first residue comprising a pyridyl ring, whose hydrogen atoms may be substituted, and a second residue comprising a carboxyl group. The first and second residues may be attached to a polymer which coats a carrier, but which polymer is not covalently grafted to the carrier. The sorbents can be used to separate or to increase the concentration and/or purity of a protein or peptide from a mixture containing the same.

20 Claims, 7 Drawing Sheets

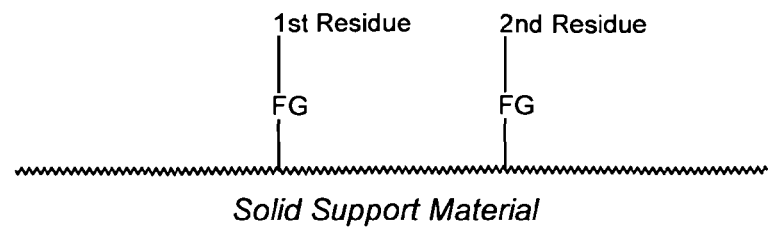
A
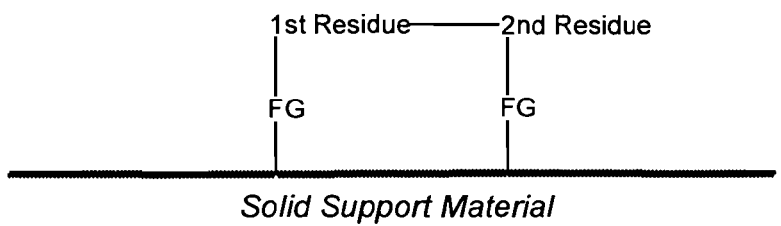
B
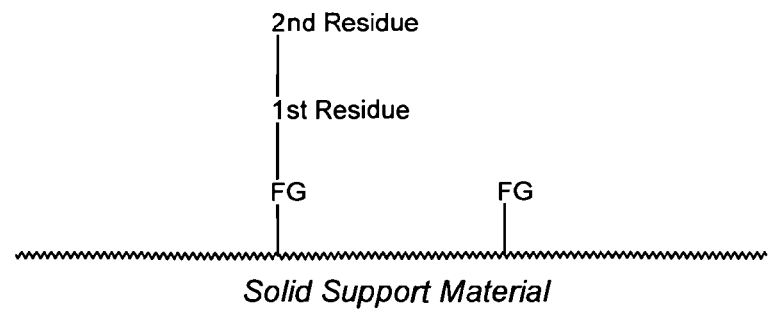
C
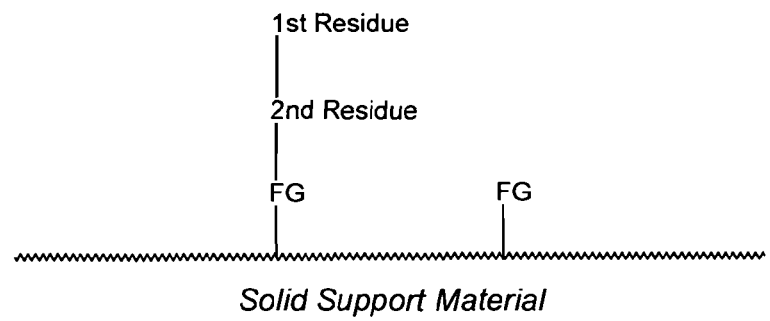
D
Figure 1: configurations A – D

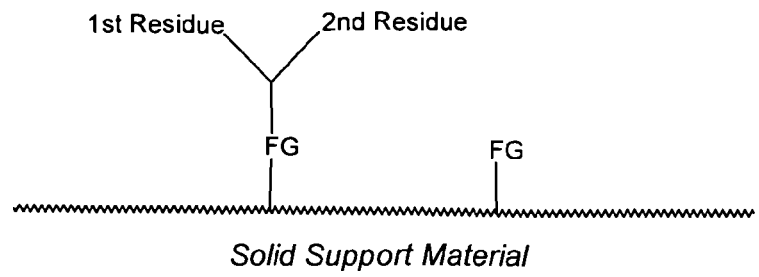
E
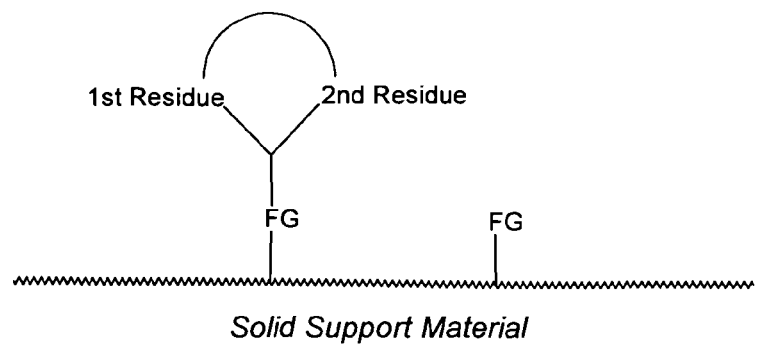
F
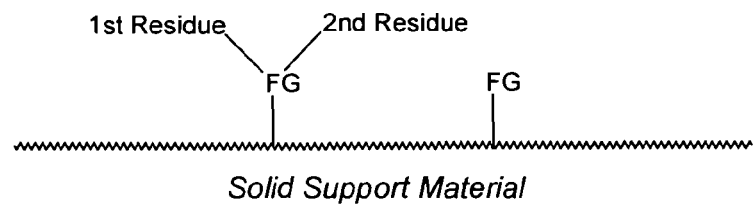
G
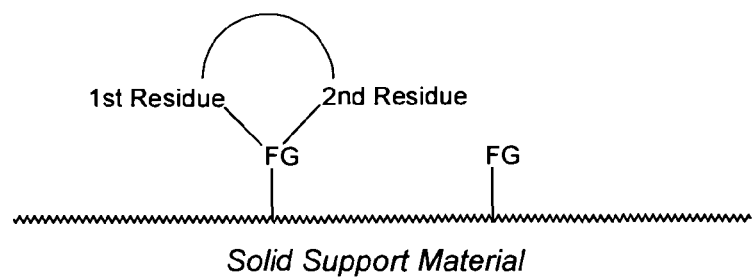
H
Figure 1 *(continued)*: configurations E –H

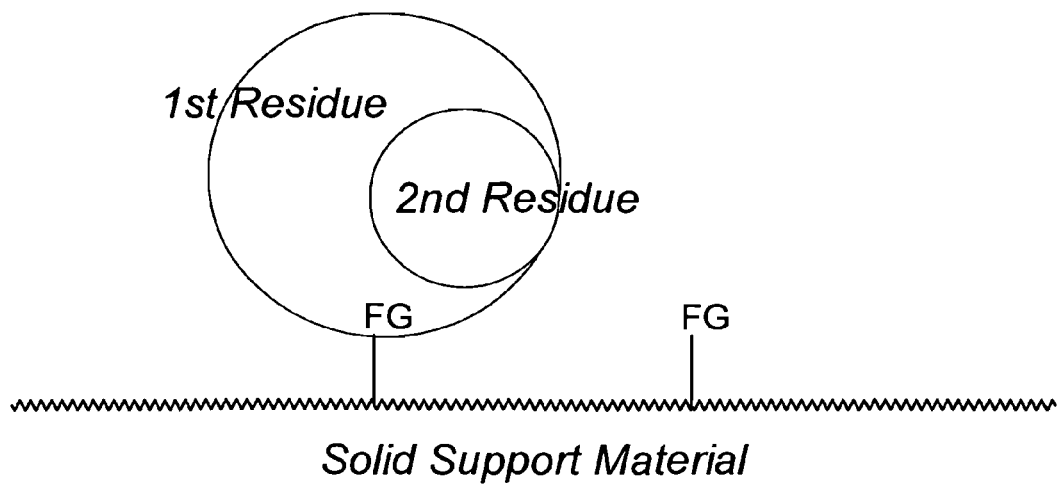
Figure 1 *(continued)*: general representation I

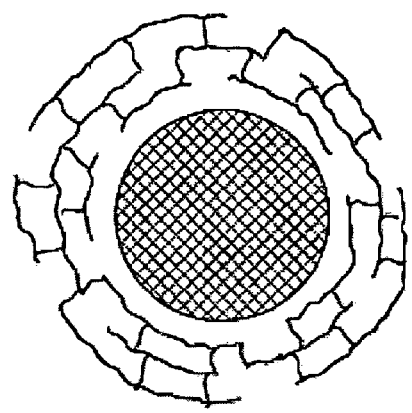
A
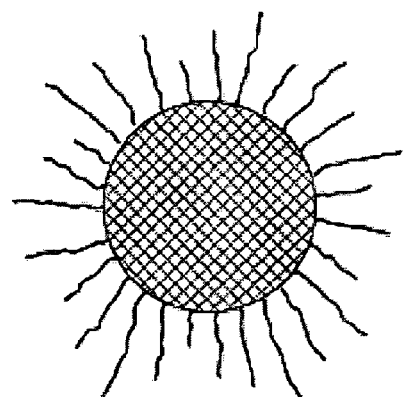
B
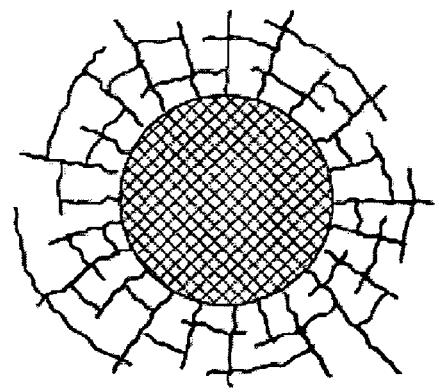
C
Figure 2

SPECIFIC SORBENT FOR BINDING PROTEINS AND PEPTIDES, AND SEPARATION METHOD USING THE SAME

FIELD OF THE INVENTION

The present patent application is related to the field of separation technology of biomolecules, in particular to biochromatography.

BACKGROUND OF THE INVENTION

Chromatography media for biomolecules have traditionally been categorised according to one or more of the following possible modes of interaction with the sample:
Hydrophobic Interaction (<<reversed phase>>)
Hydrophilic Interaction (<<normal phase>>)
Cation Exchange
Anion Exchange
Size Exclusion
Metal Ion Chelation Perpetual improvements in the titres of technical fermentation processes led to an increased demand of simple, cost-effective, and highly selective downstream purification technologies capable of handling large protein capacities without up-scaling the required volumes of liquid by the same factor. Traditional stepwise application of the above chromatographic categories to a given separation problem was accordingly mirrored in a step-by-step, steady improvement of the product purity but also in product losses at every stage which accumulate seriously in the end, not to mention the operational time and cost of goods. Introduction of affinity chromatography at an early stage into the downstream process could be an answer to this demand since the reduction of a consecutive series of sequential chromatography steps into only one could thus be demonstrated many times. Affinity chromatography is sometimes regarded as a class of its own although, from a chemical point of view, it is based on the same interaction modes as above, but usually on a combination of two or more modes. The principal characteristic of affinity chromatography is its high specificity of a pre-determined analyte which is usually based on a known molecular recognition pair of biological significance such as antigen-antibody, carbohydrate-lectin, hormone-receptor, or between complementary nucleic acid strands. Most affinity sorbents are therefore made-to-measure by the end-user according to his particular separation task. To yield a fully functional sorbent, the biological affinity residue is coupled—immediately or via an optional tether allowing more degrees of freedom in the translational and rotational motion of the residue—by a choice of only a few standard bioconjugation techniques to a support material which itself may be commercially available. The shelf-life of such a sorbent is normally only short, and it has often to be prepared on-demand.

Additionally, synthetic affinity ligands such as short linear or cyclic synthetic peptides or peptidomimetics, but also certain reactive dyes (mainly triazine dyes) have been found to interact group-specifically with biomolecules. The latter are inexpensive and easy-to-prepare low-molecular weight residues which lack the disadvantages of the labilities and variabilities in the tertiary structures of biopolymers. Moreover, due to their small molecular sizes and tunable, robust activation chemistries, they can be efficiently immobilised in a directed orientation onto solid supports even without long tethering, whereas biopolymers under the same conditions often suffer from lack of activity after immobilisation due to defolding, steric hindrance, or random orientation. In either case, the component of the sorbent which is actively involved in the recognition process is usually only present on the surface (often as a surface-bound monolayer) of a supporting solid.

Apart from homogeneous solid support materials, sorbents consisting of a 2-layered cross-sectional morphology according to the general scheme of a bulk solid support material whose surface is covered with a thin film of a crosslinked polymer are well-known from the state of the art. Polymers such as heavily (radiation-)crosslinked polybutadiene, polystyrene, polysiloxane, poly(meth)acrylate, and polyamides have primarily been used in the past. They have been employed primarily with the intent of creating a dense interface which shields the surrounding medium from unwanted interactions with the underlying part ("carrier") of the solid support material. Such interactions may lead to unspecific or even irreversible binding of biomolecules to the sorbent while, on the other hand, constituents of the solid support material or its chemical linkages to the residues may be corroded by aggressive components of either the sample or the eluent. Polymer-coated sorbents are basically known for applications in all chromatographic categories as they are listed above, but in particular for hydrophobic interaction and size exclusion. Also known are polymer coatings which are not internally crosslinked but grafted to the carrier material as linear or branched chains, such as the so-called tentacle resins.

Affinity chromatography, on the other hand, has mostly been carried out with bulk gel-phase resins. Pre-eminent gel-forming materials are medium-crosslinked polysaccharides, polyacrylamides, and poly(ethylene oxides). Such hydrogels ensure a biocompatible interface which can well accommodate both the active residue and the biological analyte interacting therewith due to their softness (conformational flexibility, elastic modulus), large pore systems, high polarity and high water content, as well as the absence of reactive or denaturing chemical groups. They are able to retain proteins in their native state, i.e. preserve their correctly folded, three-dimensional structure, state of association, and functional integrity. This is to a large part a consequence of the fact that organic solvents which are often required to elute proteins or peptides from strongly adsorbing, hydrophobic (<<hard>>) media, can be avoided. Lack of intrinsic adsorption strength of the support is thereby compensated by the introduction of highly-specific, intact biological ligands as binding partners for the separation target which are well accommodated within the hydrogel. The mechanical resistance of these media is, however, much weaker than that of inorganic support materials since they are compressible under an applied pressure and do not tolerate shear stress caused by agitation, column packing or high liquid flow rates. Affinity sorbents that are fully compatible with robust HPLC process conditions are therefore rare.

Only in the recent past it has been recognised that the mechanical resistance of the stationary phase is a bulk property of the sorbent support whereas only a thin layer at the interface between the stationary and the mobile phases is responsible for mass exchange and for the interaction with the biological analyte. Therefore the concept of combining the function of a mechanically very rigid and dimensionally stable, porous 3-dimensional core, and a biocompatible, gel-like interface layer which carries the active residues for binding the analyte has been brought up, and the associated synthetic problems have been technically solved. Such hybrid materials employ loosely crosslinked polymers of high polarity on a base of either an inorganic oxide or a densely crosslinked polymer of low polarity.

Methodologically, they can be prepared by applying the polymer of high polarity onto the core material or by directly polymerising polar monomers, precursors thereof or a prepolymer in the presence of the core material and a crosslinker. The majority of materials prepared according to the latter method is being described in the literature as having either a non-pore-penetrating or a pore-filling morphology. While non-penetrating films suffer from restricted surface areas available for interaction with the analyte and thus low binding capacities which only depend on the thickness of the polymer film, pore filling films take advantage of the full inner pore volume of the core material in the interaction with an analyte, which usually results in good binding capacities but slow diffusional mass transfer rates inside the pores and exchange kinetics with the mobile phase. A polymer film covering, but not filling completely, the interior surfaces of the core material, would be beneficial in this respect. The best known representative of this whole class of sorbents is the system which consists of branched and optionally further crosslinked polyethylene imine grafted onto a porous silica support core material. It has been demonstrated that such sorbents can be further derivatised but they have been commercialised only for ion exchange and those group-specific affinity applications which require only small standard residues.

A conceptually different approach to the production of synthetic affinity media is the so-called <<molecular imprinting>> technique which is based on shape and functional group complementarity between the target substrate and polymeric cavities formed during a polymerisation reaction which is carried out in the presence of the target substrate and a porogen, which have to be removed subsequently. Imprinting has been developed for a large number of substrates including proteins and peptides, and can be split in a covalent and a non-covalent method, as far as the temporary fixation of the target is concerned. It is, however, restricted to the formation of a few highly-crosslinked types of polymers as solid support materials and has so far not found widespread acceptance once the production scale is reached, especially not for pharmaceutical proteins or peptides which are under the control of a regulatory body.

The most widespread used affinity media for the purification of immunoglobulins G (IgG) are support-bound proteins A or G, both of which are naturally produced on the cell walls of Staphylococci, as well as protein L, but all require rather high capital investments for large-scale applications, which basically prevent their use as disposables. Protein A is known to bind a particular epitope on the constant Fc part of antibodies. It is therefore of limited use in the purification of recombinant antibody fragments or fusion products lacking this region. Repeated use of protein-derived sorbents is, on the other hand, associated with the disadvantages of protein secondary/tertiary structure and/or chemical linkage instability towards harsh manufacturing conditions, resulting in possible inactivation or leakages especially during obligatory, strongly alkaline sanitisation treatments in between chromatographic runs. In addition to an accordingly reduced lifespan there is an ongoing debate as to the application of protein A sorbents in pharmaceutical production since even minute amounts of leaked protein A are suspected to cause immunological disorders in humans when products to be purified are for in vivo pharmaceutical use. Thus, registration approval and expected market authorisation for a regulated product are other important factors in the decision for a technical purification process, and therefore it has become an industry standard that protein A chromatography must be followed by an additional chromatography step in order to remove leached toxicants.

Beside attempts of creating engineered variants of these proteins with improved technical properties, as a consequence also a few sorbents having either very short (unnatural) peptide epitopes only or even fully synthetic residues were manufactured. Those synthetic media useful as protein A/G/L alternatives which are commercially available have recently been reviewed in the January 2007 issue of *Journal of Chromatography B*, volume 848.

BACKGROUND ART

The usefulness of pyridyl rings as well as carboxyl groups and their—through protonation-deprotonation equilibria—ionisable forms, exemplarily investigated for the prototypical structures of formulae I and II, as residues of biochromatography sorbents has been recognised earlier but independently and without claiming the benefits of their combined use. However, examples of residues comprising carboxyl groups are found more often in the scientific and patent literature within the context of weak cation exchangers than residues comprising pyridyl rings. An obvious way of introducing a carboxyl group into a sorbent is by way of amide bond coupling with the natural amino acids aspartic acid or glutamic acid or a protected form thereof, with or without an additional linker moiety. With both amino acids, two options for coupling to the support by solid-phase synthesis techniques are feasible: coupling through amide formation at the amino group, resulting in a structure still containing two dissociable carboxyl groups, or alternatively through amide formation at either of the two carboxyl groups resulting in a structure still containing a protonable amino group as well as one dissociable carboxyl group. All these different possibilities have already been realised experimentally. In the following, three representative pieces of prior art are presented.

In international patent application WO 00/69872 (Promega Corporation), pH dependent ion exchange matrices are provided, with methods for making such matrices, and methods for using such matrices to isolate a target nucleic acid, as such as plasmid DNA, chromosomal DNA, or RNA from contaminants, including proteins, lipids, cellular debris, or other nucleic acids. Each pH dependent ion exchange matrix of the invention comprises at least two different ion exchange functional groups, one of which is capable of acting as an anion exchanger at a first pH, and the other of which is capable of acting as a cation exchanger at a second, higher pH. The matrix has an overall neutral charge in a pH range between the first and second pH. The pH dependent ion exchange matrices of the present invention are designed to bind to the target nucleic acid at a pH wherein the overall charge of the matrix is positive, and to release the target nucleic acid as the pH of the surrounding solution is increased.

International patent application WO 98/08603 (Upfront Chromatography A/S) relates to a method for the isolation or purification of immunoglobulins from a solution containing immunoglobulins, e.g. hybridoma cell culture supernatants, animal plasma or sera, or colostrum. The method includes the use of a minimum of salts, such as lyotropic salts, in the binding process and preferably also the use of small amounts of organic solvents in the elution process. The solid phase matrices, preferably epichlorohydrin activated agarose matricees, are functionalised with mono- or bicyclic aromatic or heteroaromatic ligands (molecular weight: at the most 500 Dalton) which may comprise an acidic substituent, e.g. a carboxylic acid.

German patent application DE 102008012224 (Lanxess Deutschland GmbH) relates to monodisperse, gel-form or macroporous picolylamine resins based on at least one monovinylaromatic compound and at least one polyvinylaromatic compound and/or a (meth)acryloyl compound which contain, as a functional group, tertiary nitrogen atoms in structures which may contain an optionally substituted picolyl radical, to a process for preparation thereof and to the uses thereof, especially use in hydrometallurgy and electroplating.

To the best of our knowledge, neither in any of these nor in any further piece of prior art from the patent or scientific literature, a sorbent according to the present invention was yet attempted to be prepared which comprised a combination of both isonicotinic amide and succinic monoamide as prototypes of residues comprising a pyridyl ring or a carboxyl group, respectively, whether contained within the same or different residues. Only in cases of incomplete derivatisation of the support, residual accessible functional groups of the support (or corresponding end-capped derivatives) have to be taken into account of playing a possible role as a further residue secondary to e.g. pyridyl ring structures. However, these functional groups are usually chemically simple moieties, and thus have to be taken only into account as second residues. Even in publications in which sorbents exhibiting one of each single residues at a time were examined, no hint was given concerning the advantages of a combined use of the two residues within the same sorbent. Moreover, only very few sorbents having either type of residue were built of a 2-component layered composite support material. Instead, residues were mostly immobilised directly or through linker moieties of low molecular weight on the bulk carrier material.

OBJECTS OF THE INVENTION

One object of the invention is to provide a novel purification method for proteins and peptides and a sorbent for performing said method.

BRIEF SUMMARY OF THE INVENTION

The present invention is directed toward a sorbent comprising a solid support material, the surface of which comprises at least two different residues among which are first residues comprising a pyridyl ring, whose hydrogen atoms may be substituted, and second residues comprising a carboxyl group. Optionally, these at least two residues are being carried by a film of a polymer covering said surface. Due to its of fully synthetic origin, said sorbent is characterised by a high physical (particularly thermal) and chemical robustness, though still allowing the specific separation of biomolecules under gentle physiological conditions, even from unfavourable sample matrices. Alternative methods for the preparation of such sorbent are also provided.

The invention also provides a method for separating, or increasing the concentration and/or purity of, a protein or peptide from a mixture containing the protein or peptide. The method comprises contacting said mixture with a sorbent according to the invention, to which the desired protein or peptide is bound, the subsequent elution of said protein or peptide from the sorbent, and optionally an intermediate rinsing step.

Disclosed are also various analytical and preparative biochemical as well as medical applications in which the sorbent and/or the method can be beneficially employed. Antibodies purified according to the method are characterised by percentages of recovery, purity, and biological activity which are comparable to those obtained via conventional bioaffinity separation techniques, without suffering from the disadvantages of such techniques.

Certain specific embodiments of the invention are disclosed below, whereby also combinations of the characteristic features of individual embodiments are imaginable and thus within the scope of the invention:

According to a general aspect, the sorbent according to the invention comprises a solid support material, the surface of which comprises first residues comprising a pyridyl ring ($-C_5H_4N$), whose hydrogen atoms may be substituted, and second residues comprising a carboxyl group ($-COOH$).

In one embodiment, the first and second residues are not connected directly with each other but are separately attached to either a bulk solid support material itself or a polymer film supported by it as a carrier. In this embodiment, the pyridyl ring and the carboxyl group are not linked to the surface of the support material via the one and same functional group.

In one aspect, the invention relates to a sorbent comprising a solid support material, the surface of which comprises a first residue comprising a pyridyl ring ($-C_5H_4N$), whose hydrogen atoms may be substituted, and a second residue comprising a carboxyl group ($-COOH$), and at least two functional groups, which may be the same or may be different from each other, via which the first and the second residue are linked to the surface of the support material, wherein the first residue and the second residue are not linked to the surface of the support material via the one and same functional group.

In one embodiment, the solid support material of said sorbent comprises a carrier the surface of which is covered with a film of a polymer comprising a first and a second functional group, which may be the same or which may be different from each other, which in turn carry said first and second, and optionally a third and a fourth residue.

In one embodiment, the first and/or second residues comprise a linker.

In one embodiment the first and/or second residues comprise a covalent, conformationally flexible linker of a length of from 1 to 20 atoms.

In one embodiment the covalent, conformationally flexible linker does not contain sulphur.

In one embodiment, the linkers comprise independently from each other from 20 to 300 carbon atoms. In said embodiment, the linker consists of or comprises polyethylene glycol moieties.

In one embodiment further substituents are bound to the pyridyl ring.

In one embodiment said further substituents are not comprising anion-exchanging (i.e., positively charged) groups.

In one embodiment, the first residues are pyridine-4-carboxamido residues (isonicotinic amide residues), whereby said residues are preferably bound to the surface of the solid support material via their amide groups.

In one embodiment the second residues are 3-carboxamidopropionic acid residues (succinic monoamide residues), whereby said residues are preferably bound to the surface of the solid support material via their amide groups.

In one embodiment the first residues are pyridine-4-carboxamido (isonicotinic amide) residues and the second residues are 3-carboxamidopropionic acid (succinic monoamide), whereby both residues are preferably bound to the surface of the solid support material via their amide groups.

In one embodiment one or more hydrogen atoms of the pyridine-4-carboxamido residues and/or the 3-carboxamidopropionic acid residues (the "residue cores") are substituted by substituents.

In one embodiment said substituents are not comprising hydrophobic groups.

In one embodiment the first and second residues are present in a molar ratio of from 1:1 to 2:1, preferably in a ratio of about 3:2.

In one embodiment the first residue comprises the second residue.

In one embodiment the surface of the solid support material additionally comprises third residues and optionally also fourth residues.

In one embodiment the third residues comprise an amine or amide structure, preferably a primary amine structure.

In one embodiment the first residues are present at a molar percentage of between 25% and 50%, based on the total molar amount of all residues present on the surface of the sorbent.

In one embodiment the second residues are present at a molar percentage of between 20% and 40%, based on the total molar amount of all residues present on the surface of the sorbent.

In one embodiment the first and second residues are present at a molar percentage of between 25% and 50% first residues and of between 20% and 40% second residues, based on the total molar amount of all residues present on the surface of the sorbent.

In one embodiment, the first, second, and third residues are present in a molar ratio of about 35:25:40.

In another embodiment, the first and second residues are present at a molar percentage of from 40 to 55% first residues and from 45 to 60% second residues, based on the total molar amount of all residues present on the surface of the sorbent.

In one embodiment the total density of all residues amounts to from $0.1 \text{ mol dm}^{-3}$ to $1.0 \text{ mol dm}^{-3}$, preferably at least about $0.3 \text{ mol dm}^{-3}$.

In one embodiment each type of residue is homogeneously and randomly (statistically) distributed on the surface of the solid support material.

In one embodiment the solid support material consists of a carrier the surface of which is covered with a film of a polymer having functional groups which are at least partially substituted with the first and second, and optionally the third and fourth residues.

In one embodiment the polymer consists of individual chains which are covalently crosslinked with each other, but which are not covalently grafted or bound to the surface of the carrier.

In one embodiment the polymer chains are covalently crosslinked with each other to an extent of from 2% to 20% based on the number of functional groups available for crosslinking.

In one embodiment the polymer consists of individual chains which are covalently grafted to the surface of the carrier, but not covalently crosslinked with each other.

In one embodiment the polymer chains are covalently grafted to the surface of the carrier via their terminal functional groups.

In one embodiment the film of the polymer accounts for from 5% to 30%, preferably from 15% to 20%, of the total weight of the sorbent.

In one embodiment the polymer is swellable in aqueous or mixed aqueous-organic media.

In one embodiment the polymer is a synthetic polyelectrolyte.

In one embodiment the crosslinking or grafting connections of the polymer and/or the linkages of the residues are made of amide, urethane, urea, or secondary/tertiary amine bonds.

In one embodiment the polymer is a partially derivatised polymer selected from the group consisting of polyvinyl alcohol, polyvinyl amine, polyallyl amine, polyethylene imine, polyacrylic acid, and polymethacrylic acid, or any copolymer or polymer blend comprising at least one of these polymers.

In one embodiment, the polymer is polyvinylamine.

In one embodiment the solid support material or at least the carrier is a porous material having a pore size of from 10 nm to 400 nm, or a specific surface area of from $1 \text{ m}^2 \text{ g}^{-1}$ to $1,000 \text{ m}^2 \text{ g}^{-1}$, or a porosity of from 30% to 80% by volume.

In one embodiment the solid support material is a particulate material having a particle size of from 5 μm to 500 μm.

In one embodiment the solid support material is a sheet- or fibre-like material such as a membrane.

In one embodiment the material the carrier is made of is different from the material the film of a polymer is made of.

In one embodiment the solid support material or at least the carrier is made of a material selected from the group consisting of generic or surface-modified polystyrene, polystyrene sulphonic acid or a polystyrene sulfonate, polyacrylates, polymethacrylates, polyvinyl alcohol, silica, glass, starch, cellulose, agarose, sepharose, and dextran, or composites thereof.

In one embodiment the sorbent additionally comprises an easily detectable tag such as an optically absorbing, an optically emitting, a radioactive, a magnetic, or a mass- or radiofrequency-encoding tag.

The invention also relates to a method for preparing a sorbent, comprising:
 (i) providing a polymer having functional groups;
 (ii) adsorbing a film of said polymer onto the surface of a carrier;
 (iii) crosslinking a defined portion of said functional groups of the adsorbed polymer with at least one crosslinking reagent;
 (iv) derivatising further defined portions of said functional groups of the crosslinked polymer with first residues comprising a pyridyl ring (—$C_5H_4N$), whose hydrogen atoms may be substituted, and with second residues comprising a carboxyl group (—COOH), and with optional further residues.

The invention also relates to a method for preparing a sorbent, comprising:
 (i) providing a polymer having functional groups;
 (ii) derivatising defined portions of said functional groups with first residues comprising a pyridyl ring (—$C_5H_4N$), whose hydrogen atoms may be substituted, and with second residues comprising a mononuclear heteroaromatic structure comprising a carboxyl group (—COOH), and with optional further residues;
 (iii) adsorbing a film of the derivatised polymer onto the surface of a carrier;
 (iv) crosslinking a further defined portion of said functional groups of the adsorbed polymer with at least one crosslinking reagent.

The invention also relates to a method for preparing a sorbent, comprising:
 (i) providing a polymer having functional groups;
 (ii) adsorbing a film of said polymer onto the surface of a carrier;
 (iii) grafting a defined portion of said functional groups of the adsorbed polymer to said carrier;
 (iv) derivatising further defined portions of said functional groups of the grafted polymer with first residues comprising a pyridyl ring (—$C_5H_4N$), whose hydrogen atoms may be substituted, and with second residues comprising a carboxyl group (—COOH), and with optional further residues.

The invention also relates to a method for preparing a sorbent, comprising:

(i) providing a polymer having functional groups;
(ii) derivatising defined portions of said functional groups with first residues comprising a pyridyl ring (—$C_5H_4N$), whose hydrogen atoms may be substituted, and with second residues comprising a carboxyl group (—COOH), and with optional further residues;
(iii) adsorbing a film of the derivatised polymer onto the surface of a carrier;
(iv) grafting a further defined portion of said functional groups of the adsorbed polymer to said carrier.

In one embodiment of the methods for preparing a sorbent, the polymer is soluble in aqueous or mixed aqueous-organic media.

In one embodiment the functional groups of the polymer are —NH—, —$NH_2$, —OH, —COOH or —COO— groups.

In one embodiment the polymer has a molecular weight of between 5,000 Dalton and 50,000 Dalton.

In one embodiment the at least one crosslinking reagent is selected from the group consisting of dicarboxylic acids, diamines, diols, and bis-epoxides.

In one embodiment the at least one crosslinking reagent is a linear, conformationally flexible molecule of a length of between 1 and 20 atoms.

In one embodiment the derivatisation step is carried out by formation of amide bonds between said functional groups and said residues.

In one embodiment the derivatisation step is carried out stepwise with each residue.

The invention also relates to a method of separating, or increasing the concentration and/or purity of, a protein or peptide from a mixture containing said protein or peptide, comprising:
(i) contacting said mixture being dissolved or suspended in a first liquid with a sorbent according to the invention or with a sorbent prepared according to a method of the invention, for a period of time sufficient to enable said protein or peptide to become bound to said sorbent;
(ii) optionally rinsing said sorbent with a second liquid;
(iii) contacting said sorbent with said bound protein or peptide with a third liquid for a period of time sufficient to enable said protein or peptide to become released from said sorbent;
(iv) optionally washing and/or regenerating the sorbent with a fourth and/or fifth liquid.

In one embodiment of the method of separating, or increasing the concentration and/or purity of, a protein or peptide, the first liquid, the second liquid, and the third liquid are buffered aqueous media, not containing further organic modifiers.

In one embodiment the second liquid is the same as the first liquid.

In one embodiment the pH of the third liquid is close to the isoelectric point pI of the bound protein or peptide.

In one embodiment the pH of the third liquid is different, in particular higher, than the pH of the first and optionally of the second liquid.

In one embodiment the pH of the first liquid is in the range of from 4.0 to 6.0 and the pH of the third liquid is in the range of from 6.5 to 8.5.

In one embodiment the ionic strength of the third liquid is different, in particular higher, than the ionic strength of the first and optionally of the second liquid.

In one embodiment the method is carried out as a membrane-filtration technique, a solid phase extraction technique or as a medium- to high-pressure liquid chromatography technique.

In one embodiment the method further comprises the isolation of the released protein or peptide from the third liquid subsequent to step (iii).

In one embodiment the released protein or peptide of step (iii) contains less than 10 ppm of leached sorbent or other leachable substances therefrom.

In one embodiment the method is combined with further separation processes such as precipitation, centrifugation, drying, (micro-/ultra-)filtration, dialysis, ion exchange, or viral reduction treatments.

In one embodiment said protein or peptide has an isoelectric point pI of from 4.5 to 8.5 and a molecular weight of from 100 to 500,000 Da.

In one embodiment said protein or peptide is a natural antibody, particularly an immunoglobulin G, a fragment or an oligomeric associate derived from an antibody, a genetically engineered antibody, or an antibody- or antibody fragment-containing fusion protein.

In one embodiment the mixture containing said protein or peptide is a crude or partially purified biosynthetic product, obtained from a microorganism or a cell culture, or from a crop extract.

The invention also relates to a column for liquid chromatography or solid phase extraction comprising a sorbent according to the invention or a sorbent prepared according to a method of the invention as a stationary phase within a tubular containment and optionally further components such as frits, filter plates, flow distributors, seals, fittings, screwings, valves, or other fluid handling or connection elements.

In one embodiment the column is further characterised by its physical and chemical resistance against applied pressures up to 20 bar, against applied heat up to 110° C., as well as against common sanitisation protocols, thus enabling its repetitive use of up to 1,000 times, preferably up to 5,000 times.

The invention also relates to a collection of a plurality of the same or different sorbents according to the invention or of sorbents prepared according to a method of the invention or of columns according to the invention in the format of a microplate or microchip array, or a multi-capillary or microfluidic device, capable of being processed in parallel.

The invention also relates to a diagnostic or laboratory purification kit comprising a sorbent according to the invention or a sorbent prepared according to a method of the invention or a column according to the invention or a collection of sorbents or columns according to the invention and, within the same packaging unit, further chemical or biological reagents and/or disposables necessary for carrying out the method of separating a protein or peptide according to the invention or a different analytical, diagnostic, or laboratory method different therefrom.

The invention also relates to the use of a sorbent according to the invention or a sorbent prepared according to a method of the invention in the manufacture of a pharmaceutical, nutritional or cosmetic composition comprising at least one protein or peptide of diagnostic, therapeutic, nutritional, or cosmetic value.

The invention also relates to the use of a sorbent according to the invention or a sorbent prepared according to a method of the invention in the removal of at least one protein or peptide, and in the medical prevention or treatment of diseases of a human or an animal being caused by the presence of said at least one protein or peptide.

The invention also relates to the use of a sorbent according to the invention or a sorbent prepared according to a method of the invention in the identification, characterisation, quantification, or laboratory purification of at least one protein or peptide.

The invention also relates to the use of a sorbent according to the invention or a sorbent prepared according to a method of the invention for the reversible immobilisation of at least one protein or peptide and optionally testing for binding of further chemical or biological structures to said protein or peptide.

According to a first aspect, the invention relates to a sorbent comprising a solid support material, the surface of which comprises
- a first residue comprising a pyridyl ring (—$C_5H_4N$), whose hydrogen atoms may be substituted; and
- a second residue comprising a carboxyl group (—COOH); characterized in that the first and second residue are not directly connected with each other but are separately attached to either a bulk solid support material itself or a polymer film supported by it as carrier.

According to a second aspect, the invention relates to a sorbent comprising a solid support material, the surface of which comprises
- a first and a second functional group, which may be the same or different;
- a first residue comprising a pyridyl ring (—$C_5H_4N$), whose hydrogen atoms may be substituted; and
- a second residue comprising a carboxyl group (—COOH); characterized in that the first residue is bound to the first functional group, and the second residue is bound to the second functional group.

According to a third aspect, the invention relates to a sorbent comprising a solid support material, the surface of which comprises
- a first and a second functional group, which may be the same or different;
- a first residue comprising a pyridyl ring (—$C_5H_4N$), whose hydrogen atoms may be substituted; and
- a second residue comprising a carboxyl group (—COOH); characterized in that the first residue is bound to the first functional group, and the second residue is bound to the second functional group; and wherein none of said functional groups is bound to both said first residue and said second residue.

According to a fourth aspect, the invention relates to a sorbent comprising a solid support material, the surface of which comprises
- a first and a second functional group, which may be the same or different;
- a first residue comprising a pyridyl ring (—$C_5H_4N$), whose hydrogen atoms may be substituted; and
- a second residue comprising a carboxyl group (—COOH); characterized in that the first residue is bound to the first functional group, and the second residue is bound to the second functional group; and wherein the first and second residue are not directly connected with each other.

In one embodiment, the first residue or the second residue or the first and the second residue are bound to said first and second functional group via a linker.

In one embodiment, from 5 to 95%, or from 20 to 90%, or from 30 to 80%, or from 40 to 70%, or from 50 to 60% of said first and second functional groups are bound to said first and second residue, and wherein said first and second residue are present in a molar ratio of from 1:1 to 2:1.

In one embodiment, the surface of the solid support material is covered with a film of a polymer comprising said first and second functional groups which in turn carry said first and second, and optionally a third and a fourth residue.

In one embodiment, a first portion of said first and second functional groups is crosslinked with at least one crosslinking reagent, and wherein a second portion of said first and second functional groups are bound to said first and second, and optional further residues.

For the purpose of this disclosure, all embodiments as listed for the sorbent according to the general aspect of the invention may be combined with the sorbent according to the first, the second, the third, and the fourth aspect of the invention.

Detailed Description of the Preferred Embodiments

The technical problem underlying the present invention can be stated as to provide a novel purification method for proteins and peptides which lacks the disadvantages of the previously known methods as they have been summarised in the foregoing sections. This means that the method should allow to isolate the targeted protein or peptide in a single step from the sample matrix at high recovery without compromising its functional integrity, while largely avoiding costly materials but still being versatile enough to be able to adhere to standard cleaning and sanitisation protocols of the equipment in use and thus ensuring acceptance of the method by the respective regulatory authorities, i.e. to provide the targeted protein or peptide in an economically feasible way in a pharmaceutical quality.

This technical problem could now be solved by providing a novel type of sorbent to be employed in a solid-liquid equilibrium distribution process of the protein or peptide to be purified, which can be distinguished from those known from the state of the art primarily by its specific two-fold chemical derivatisation with residues, said derivatisation being tailored to the problem of separating the targeted proteins or peptides from their side products, particularly from various other proteins or peptides, with a selectivity and sensitivity that can match that of conventional affinity media but having a composition which is completely devoid of delicate biological material which may be expensive to manufacture and/or degrading under harsh conditions. High durability of all materials employed in the production of the sorbent also ensures long-term reproducibility of any separation method which uses the sorbent, which may become obvious by the absence of drift effects in analysis results.

Of assisting help in the solution of the technical problem given above is a layered assembly of the sorbent comprising at least two different materials of which one is a synthetic or biosynthetic polymer film carrying both residues and covering the second material which serves as a solid base. This particular assembly is characterised on the one hand by a comparatively high weight content and high physical stability of the polymer film, but still a rather high degree of chain flexibility resulting also in high solvent and sample uptake capacity as well as their fast diffusional exchange. The film is thus maintained in a homogeneous, biocompatible, soft and gel-like state. This allows the analyte protein or peptides to immerse with their partial or full molecular volumes into the layer containing those active elements of the sorbent responsible for binding and migrate either through it or along its surface while simultaneously preventing their denaturation. It thus ensures the creation of a quasi-three-dimensional interaction space for the analytes and allows multi-point contacts between epitopes distributed over the entire protein or peptide surface and the residue-modified gel phase. Sample components are thereby also effectively shielded by the polymer film from unwanted interactions with the underlying constituents of the solid support material.

With the intent to assess the entire scope of the present invention and to render it more precisely, the meaning of a number of terms as used within the context of the present invention hereafter is first being defined in the subsequent paragraphs. It has to be understood that all examples are given for illustrative purposes only and not meant as an exclusive list of embodiments. Persons skilled in the art will certainly recognise additional and analogous ways of carrying out the invention without deviating from its overall spirit. The schematic representation of FIG. 6 again symbolises the interrelationship between a number of different terms used herein which are related to the sorbent composition.

The term "sorbent" means any synthetic or biosynthetic material for use as a stationary phase in a solid < > liquid equilibrium distribution process of a sample, which exhibits selective non-covalent binding properties as a receptor for at least one given target protein or peptide contained in said sample, or which is capable to distinguish in its non-covalent binding properties between at least two given target peptides or proteins of different constitution contained in said sample (i.e. high absolute binding constant or high binding constant difference). It is therefore specially designed to solve a given analytical or preparative detection, separation, immobilisation, or (bio)chemical conversion task which often consists of a unique combination of at least one target protein or peptide, whose constitution may be known, partly known, or unknown, and a sample matrix, whose composition may similarly be known, partly known, or unknown.

As opposed to generic phases (which differentiate analytes according to cumulative parameters which are basically averaged over the entire analyte molecule such as electrostatic charge, dipole moment or lipophilicity), such a sorbent binds, at least in part, by the concept of group complementarity to at least one domain (epitope) on the three-dimensional molecular surface of the at least one target protein or peptide. This novel concept therefore also reaches beyond the scope of so-called mixed-mode sorbents which—in a traditional meaning—separate according to a combination of two of the classical averaged effects. The sorbents of the present invention are thus designed on the molecular level to bind only a single protein or peptide or a group of structurally closely related proteins or peptides with high affinity and high individual or group selectivity out of an environment which may contain a large spectrum of different side products.

As a "solid support material" all non-porous or preferably porous, adsorptive media known to those skilled in the art such as all kinds of inorganic mineral oxides like silica, alumina, magnesia, titania, zirconia, florisil, magnetite, zeolites, silicates (celite, kieselguhr), mica, hydroxyapatite, fluoroapatite, metal-organic frameworks, ceramics and glasses like controlled pore glass (CPG), metals such as aluminium, silicon, iron, titanium, copper, silver, gold, and also graphite or amorphous carbon, paper, (bio)polymer resins such as polysaccharides, polyacrylamides, polystyrenes like Amberchrom™ etc., whether of spherical or irregular shape, can be used for building up the sorbent. Poly(styrene-co-divinylbenzene) (especially poly(styrene-co-divinylbenzene) which is bulk- or surface-sulphonated as it is used in strong cation exchange resins), polyacrylates, polymethacrylates, polyvinyl alcohol, silica, glass, and polysaccharides such as starch, cellulose, cellulose esters, amylose, agarose, sepharose, mannan, xanthan and dextran are the preferred solid support materials. The introduction of a solid base of a minimum rigidity and hardness as an insoluble support function provides a basis for the enlargement of the interface between stationary and mobile phases which is the place of interaction with the protein or peptide as the molecular basis for the process of its partitioning between said phases, and for an increased mechanical strength and abrasiveness, especially under flow and/or pressurised conditions. Solid support materials according to the invention may be of homogeneous or heterogeneous composition, and therefore also incorporate materials which are composites of one or more of the materials mentioned above, in particular multi-layered composites. In this context, magnetic particles are specifically mentioned.

In an important embodiment related hereto, the surface of the solid support material may be covered by a polymer film. Such an optional film is considered as a part of the solid support material since all preparation and separation methods developed and introduced here which rely on functional groups or residues on the immediate surface of a unitary bulk solid support material likewise work with respective functional groups or residues of such a polymer overlayer. Furthermore, a meso- or macroporous topography inherent to the bulk solid support material will often be preserved in the coating process. If in such a resulting hybrid material the surface polymer film has to be distinguished from all the material(s) underneath for purposes of the invention, the latter is summarily referred to individually as a "carrier", or, in other words, the hybrid solid support material would comprise both the carrier and the polymer film. In practice however, such a distinction is often viable only if the history of the sorbent preparation is known. The carrier as the part which provides the rigid framework of the sorbent is analogously of solid physical condition and may consist of any of those materials listed above as solid support materials which can likewise be employed according to the invention as a bulk solid support material without having a surface polymer film on top or as a carrier for such a surface polymer film. All characteristics, options, and restrictions as they have been stated above except for the suitability for adsorption of a polymer therefore apply equivalently to both terms. A central embodiment of the invention is therefore a sorbent wherein the solid support material consists of a carrier the surface of which is covered with a film of a polymer having functional groups which is at least partially substituted with the first and second, and optionally the third and fourth residues.

If, as preferred, a porous material is used as carrier, the polymer film will normally cover both its external and its mostly larger internal surface homogeneously. A "surface" thus characterises the entire solid-liquid phase interface of the sorbent during its preparation and application as a separation agent, where the recognition and binding of analytes by the residues occurs, and which is accessible to at least one dissolved protein or peptide via (optionally pressurised) hydrodynamic flow, convection, perfusion, diffusion, or electromigration, or combinations of any of these. Due to possible swelling of carriers comprising soft matter and especially of surface polymer films in proper liquids, this is not a sharp boundary but may involve an intermediate gel-phase layer. Surface properties of the sorbent may be different from the bulk properties of the materials employed. This is particularly true if two different materials are used as a carrier and a polymer film, and if preparation methods are used which lead to extraordinarily large specific surface areas.

"Covering" can be technically achieved by all means of coating known to a skilled person which may either occur under natural driving forces or be manually enforced such as spontaneous adsorption, vapour phase deposition, polymerisation from the liquid, gas or plasma phase, spin coating, surface condensation, wetting, soaking, dipping, brushing, spraying, stamping, evaporation, application of electric fields or pressure, as well as all methods based on molecular self-assembly such as, for example, liquid crystals, Langmuir- Blodgett- or layer-by-layer film formation. The polymer film may thereby be coated directly as a multilayer or as a stepwise sequence of individual monolayers on top of each other. As long as macromolecules are concerned, single- or multi-point-"adsorption", whether spontaneous or artificially accelerated, is in any case considered as being the first (incomplete) step of any coating process starting from a polymer solution which is in physical contact with the surface of a solid. It requires the presence of some at least weakly attractive physical (van der Waals-) or—in case of complementary functionalisation present on the carrier and/or the polymer—rather specific, non-covalent chemical forces between the solid surface and each single polymer strand and, if multilayers are adsorbed, also between the polymers within the same and different vertically stacked layers in order to form at least a meta-stable aggregate. Electrostatic forces between charges of opposite sign are often utilised for this purpose, the surface charge of the carrier thereby being given by its zeta potential. Initial adsorption may occur in a loose and irregular fashion which may later transform into a larger degree of two- or three-dimensional order and/or density. This is may be ascribed to some residual mobility of the polymer strands on the surface as a consequence of a steady-state equilibrium between adsorption and desorption processes at individual surface sites and may for example be fostered by annealing. It is usually necessary to further increase the stability of the adsorbed aggregate by the following introduction of covalent bonds between proximate functional groups, in addition to a basic steric (entropic) stabilisation by physical entanglement of the chains. For achieving still increased stabilities, the chains of the polymer film may further be covalently grafted to the carrier material underneath.

The external surface of the solid support material thereby may be flat (plates, sheets, foils, disks, slides, filters, membranes, woven or nonwoven fabrics, paper) or curved (either concave or convex: spheres, beads, grains, (hollow) fibres, tubes, capillaries, vials, wells in a sample tray). The pore structure of the internal surface of the solid support material may, inter alia, consist of regular, continuous capillary channels or of cavities of irregular (fractal) geometry. Microscopically, it can be smooth or rough, depending on the way of manufacture. The pore system can either extend continuously throughout the entire solid support material or end in (branched) cavities. The rate of a protein or peptide's interfacial equilibration between its solvation in the mobile phase and its retention on the surface of the stationary phase and thus the efficiency of a continuous flow separation system is largely determined by mass transfer via diffusion through the pores of the solid support material and thus by its characteristic distribution of particle and pore sizes. Pore sizes may optionally show up as asymmetric, multimodal and/or spatially (e.g. cross-sectionally) inhomogeneous distributions. Typical pore sizes of porous solids suitable for use in the invention as either full solid support materials or carriers range from 10 nm to 400 nm and can thus be categorised as meso- or macroporous; typical particle sizes of particulate materials range from 5 µm to 500 µm. Suitable solids have acceptable porosities in the range of 30% to 80% by volume and typical specific surface areas in the range from $1 \text{ m}^2 \text{ g}^{-1}$ to $1,000 \text{ m}^2 \text{ g}^{-1}$.

Alternative, more recently introduced solid support materials are the so-called monolithic chromatography media which are cast as a single macroscopic entity of the desired (usually rod-like) shape as opposed to classical compressible column packings made of loose microscopic particles. Monolithic columns can consist of silica or polymeric materials such as, for example, polymethacrylates, and their microstructure can contain fibrous capillaries or sintered particle agglomerates.

The term "film of a polymer" or "polymer film" means a two- or preferably three-dimensional synthetic or biosynthetic polymer network of at least one layer, usually between a few and a few ten molecular layers. Such a (derivatised or underivatised) polymer network may itself be prepared according to procedures known to a person skilled in the art. The film of a polymer may be of a chemically homogeneous composition, or it may be comprised of at least two different kinds of interpenetrating polymer chains (e.g., polyacrylic acid and a polyamine), either irregularly entangled or in an ordered fashion (layer-by-layer). The term "chain" generally refers to the longest continuous main strand and also possible branches of a polymer, along which functional groups are attached. The term is used both to indicate the full backbone length of a dissolved, adsorbed or grafted polymer as employed during sorbent preparation, as well as to indicate the chain segments located between the knots of a crosslinked polymeric mesh, since in the latter case the full length of individual strands is hard to identify.

"Polymers" containing at least one functional group within their backbone or side chains are preferable since they allow an easy derivatisation with residues at such functional groups in homogeneous or heterogeneous media. Furthermore, many properties of a polymer in the solid or dissolved state and also its tendency to adsorb spontaneously onto and adhere permanently to a given solid carrier are being determined by its functional groups. Polyelectrolytes are specifically mentioned here. Co-polymers, whether of alternating, statistical, or block sequence, containing both functional and non-functional units are also realisable in this respect. The preferred functional groups are primary and secondary amino, hydroxyl, and carboxylic acid or ester groups. Depending on the acidity/basicity of the surrounding medium, amino groups may be present as protonated ammonium ions, carboxyl groups as deprotonated carboxylate ions. If a porous or non-porous bulk polymer is also used as the carrier of the solid support material, it is pointed out that the film of the polymer coated thereon, as described here, will have a different chemical composition. These differences may result from the presence, kind, or density of the functional groups listed below, from lower molecular weights, or from a lower degree of crosslinking. All these parameters add to increased hydrophilicity, solvent swellability/diffusion, and biocompatibility, as well as to diminished unspecific adsorption on the coated surface.

Both natural as well as synthetic polymers may be employed in the sorbents according to the invention. Synthetic polymers are preferred.

The preferred polymer film comprises at least one polymer containing amino groups. Polyvinylamine is strongly preferred. Other suitable polyamines may comprise polyethylene imine, polyallylamine etc.

Other suitable polymers are functional polymers other than those containing amino groups, such as polyvinyl alcohol, polyvinyl acetate, polyacrylic acid, polymethacrylic acid, their precursor polymers such as poly(maleic anhydride), polyamides, or polysaccharides (cellulose, dextran, pullulan etc.). If co-polymers are employed, the preferred co-monomers are simple alkene monomers or polar, inert monomers like vinyl pyrrolidone. Preferred molecular weights of the polymers used range from, but are not limited to, 5,000 Dalton to 50,000 Dalton, which is particularly true for polyvinylamine. Polymers having a molecular weight near the lower limit of the range given above have shown to penetrate even narrow pores of the carrier so that solid state materials with high surface areas and consequently with good mass transfer kinetics, resolution and binding capacity can be used in the sorbents of the present invention.

The polymer will be adsorbed and then crosslinked or grafted as a thin adlayer onto the surface of a suitable carrier, either before or after derivatisation with first and second residues, or in between the derivatisation step with first residues and the derivatisation step with second residues. The film content of the resulting hybrid material, including its derivatisation with residues, may range from about 5% to 30%, preferably from about 15% to 20% by weight, based on the total weight of the sorbent. The exact value of the polymer content of the fully functional sorbent will also be dependent on the degree of derivatisation, the molecular weight of the residues, and the specific weight of the chosen carrier. These values correspond to a film thickness in the lower nanometer range. The coated polymer can still retain its ability to swell or shrink, the actual film thickness thereby being strongly dependent on the type of solvent being used.

The degree of crosslinking of the polymer film may range from 2% to 20%, based on the number of functional groups available for crosslinking, respectively. Particularly preferred are crosslinkages by functional group condensation, but all other methods known in polymer chemistry, including radical and photochemistry, can be applied. However, crosslinking bonds can also be formed directly between the functional groups of the polymer(s) involved without addition of crosslinking reagents. This is in particular possible if co-polymers or blended polymers are employed which provide at least two different functional groups that exhibit a latent reactivity toward each other, e.g. amine groups and carboxylic acid groups which can form amide bonds between each other after activation. Preferred crosslinks involve formation of covalent C—N bonds, e.g. amide, urethane, urea or secondary/tertiary amine bonds, and may be formed via reaction of either activated carboxylic acids or epoxides with amines. Crosslinks can alternatively be of non-covalent nature, making use of ion pairing between oppositely charged functional groups or with the help of multiply-charged counterions etc.

As used herein, the "degree of crosslinking" is given as the maximum number of crosslinks to be formed in the crosslinking reaction based on the total number of functional groups available for crosslinking. If, as preferred, bifunctional reagents are used for crosslinking, the degree of crosslinking therefore reflects the molar ratio between the amount of crosslinking reagent, which is submitted into the crosslinking reaction, and the number of polymer functional groups available for crosslinking (in such case two functional groups are required per formation of one crosslink) whereby it is assumed that the reaction proceeds nearly quantitatively at the ratios attempted here. In principle, it is possible that both inter-strand and intra-strand crosslinks as well as non-crosslinking end-terminated side chains (from partially reacting crosslinkers) are being formed.

Conversely, the term "grafting" means a covalent anchorage of single polymer chains to the surface of a solid carrier, preferable formed with functional groups thereon. It would be sufficient if each polymer strand is anchored at at least one arbitrary position along its chain. Better stabilities of the film can be achieved via multi-point grafting so that protruding polymer loops are formed on the surface. The latter method, however, reduces the three-dimensional flexibility of the polymer chains. Single-point attachments are preferably realised through a chain terminus so that the full elongated length of the chain along which preferentially a plurality of functional groups/residues or only a single one at the opposite terminus may be attached, can point outwards away from the surface. Although the actual conformation of the grafted polymer may be a random coil, the use of high grafting densities on the surface and appropriate solvents can lead to swelling and oriented self-assembling phenomena between neighbouring chains via dispersive interactions such as in the formation of polymer brushes which may be further stabilised by crosslinking. Preferably, grafting is achieved via mild condensation reactions similar to the crosslinking reactions, but methods involving propagating free radicals, ions, or radical ions such as oxidative or radiation-induced methods could also be applied. The chosen method will depend on the ease, type, and degree of functionalisation of the carrier. Grafting can be achieved in principle via two different techniques: the first technique uses surface-bound monomers or initiators to build up parallel polymer chains by in situ-polymerisation from the surface, whereas in the second technique a polymer chain is first synthesised in its full length in a homogeneous medium, i.e. in the absence of the surface, to which it is only subsequently grafted in an extra step. The latter technique is preferred if a sorbent of the invention is prepared via grafting procedures and constitutes a methodical embodiment of the invention.

In a preferred embodiment of the present invention, the polymer film, also if internally crosslinked by covalent bonds, is not grafted, i.e. covalently linked, to the carrier material underneath, i.e. it is bound thereon by physical and/or chemical adsorption only. Accordingly, the term "binding" encompasses physical and/or chemical adsorption. The chemical and mechanical stability of the composite material then results from total physical entanglement of the carrier by the crosslinked polymer film. The thickness and density of the polymer film are still sufficient in order to shield very polar or reactive groups on the surface of the supporting carrier, such as phenyl or sulphonate groups in the case of solid polystyrene sulphonate, from accessibility which are otherwise suspected to be cleaved by reagents or to undergo undefined, irreproducible or irreversible interactions with the target protein or peptide or its concomitant impurities of the mixture to be separated.

In a further embodiment, the polymer film is grafted onto the carrier but not internally crosslinked. As a third option, the polymer film may be internally crosslinked as well as grafted onto the carrier. All three different resulting network morphologies of the polymer film are depicted schematically in FIG. 2. Case A of FIG. 2 symbolises the preferred sorbent wherein the individual polymer chains are covalently crosslinked with each other but not covalently grafted to the surface of the carrier. Case B represents a sorbent wherein the individual polymer chains are covalently grafted to the surface of the carrier but not covalently crosslinked with each other. Case C represents a sorbent wherein the individual polymer chains are both covalently grafted to the surface of the carrier and covalently crosslinked with each other, as a result of a combination of the two fixation techniques (which may be carried out in any order).

The term "functional group" means any simple, distinct chemical moiety belonging to an (underivatised) solid support material or restricted to an optional polymer film on its surface, or to a polymer during preparation of said surface via film adsorption, which may serve as chemical attachment point or anchor and which therefore is, at least in the swollen state of the solid support material or a polymer film covering it, amenable to liquid or solid phase derivatisation by chemical addition or substitution reactions and optionally also to crosslinking. Functional groups will therefore typically contain at least one weak bond and/or one heteroatom, preferentially a group behaving as nucleophile or electrophile. Less reactive functional groups may need to be activated prior to derivatisation. They can thus both form the structural link between the polymer strands and the residues of the sorbent as well as forming the knots of a crosslinked network. Opposed to residues, functional groups are primarily not designed to interact with analytes (although it indeed cannot be rigorously excluded that they nevertheless do interact or aid in the separation process via repulsion of side components) but rather to provide a surface coverage with molecularly-sized spots of defined chemical reactivity that can be converted into the actually interacting residues (derivatisation) or used in the formation of covalent connections (polymer crosslinkage and grafting). The terms "connections" or "linkages" as used herein shall cover both directly formed covalent bonds as well as an extended series of covalent bonds in a row via a sequence involving multiple atoms. Other chemical moieties down to simple diatomic molecular fragments which may be present on the sorbent or an analyte and which do not fulfil either of these known and specified functions, are simply named "groups".

A set of functional groups can be treated as a plurality of separate, but identical units, and their chemical behaviour will mainly be determined by predictable and reproducible group properties only and to a far less extent by the materials to which they are attached, or their exact position on these materials. Among such functional groups are, just to mention a few, amino groups, hydroxyl groups, thiol groups, carboxylic acid groups, or carboxylic ester groups. Functional groups represent an integral part of the solid support material and are thus distributed uniformly over large areas of its surface. Suitable functional groups often exhibit weak acid or base properties and thus give a film-forming polymer the character of an ampholyte. Functional groups in a polymer can either be introduced during polymerisation from the corresponding monomers or by subsequent functional group conversion (polymer-analogous reaction) before or after adsorption onto the carrier. A polymer film can also contain two or more different functional groups either if different monomers are co-polymerised, if functional group conversion is stopped before completion, or if different polymers are layered on top of each other or as interpenetrating networks. The preferred functional groups are primary and secondary amino groups. Particular preference is given to primary amino groups.

The term "derivatisation" means any chemical reaction capable of introducing specific residues onto the surface of a solid support material or into a polymer used for covering said surface during sorbent preparation in order to produce an intermediate or fully functional sorbent, particularly by addition to, or substitution of, its functional groups with a suitable derivatisation reagent containing the residue or a precursor thereof. Interconversion of a functional group into a different but still reactive functional group shall also be covered by the term. A "precursor" of the residue may incorporate a masked or protected chemical moiety which can be deprotected or otherwise converted into the final residue after or simultaneously with the formation of a linkage with the surface or polymer in the derivatisation step. For example, if the polymer contains primary or secondary amino functional groups and derivatisation is made through amide bond formation with these, additional primary or secondary amine moieties to be contained in the residue should initially be protected as e.g. Boc- or Fmoc-derivatives in the derivatisation reagent. Further, if the bond to be formed during the derivatisation reaction between a surface or polymer functional group and a reactive center on the derivatisation reagent leads to the formation of a new chemical moiety which plays a role in the recognition of the target protein or peptide, the respective residue will apparently only be fully developed after derivatisation, and only a part or a functional modification of it is contained as a precursor in the derivatisation reagent. In such case, part of the precursor moiety (a leaving group) may also be split off during the derivatisation reaction (such as a water molecule during a condensation reaction).

Derivatisation is in each of at least one or optionally multiple steps always being carried out on a "defined portion" of the functional groups. This means that—taking the reactivities of different functional groups and reagents into account—a targeted, predetermined percentage of each given kind of functional groups present in the underivatised polymer or solid support material is always being converted into functional groups derivatised with the respective residues chosen. In order to yield homogeneously and reproducibly derivatised sorbents, calculated appropriate amounts of derivatisation reagents are then let to react with the polymer. Full derivatisation (degree of derivatisation=100%) can also be attempted, whereby the derivatisation reagent is often used in excess, but this is not a must-have.

Since the residual materials of the sorbent as such shall not be impaired during the derivatisation step, it is often desirable to perform the derivatisation under mild conditions. It may thus be necessary to either activate the functional groups or the derivatisation reagent prior to or concomitant with the actual bond formation step in order to maintain sufficient reactivity under such conditions. Preferably, the derivatisation reagent is activated. A preferred derivatisation reaction will involve a nucleophilic polymer containing electron-rich nitrogen functional groups such as amino groups and an electrophilic reagent containing a leaving group attached to an electron-poor carbon such as a carbonyl or carboxyl derivative, or vice versa. Activation can therefore be achieved by standard techniques of solid phase or liquid phase peptide synthesis, e.g. via activated esters. Preferred derivatisation reactions involve the formation of amide, urethane, urea or secondary/tertiary amine linkages with the functional groups. Due to the asymmetry of amide and urethane linkages with respect to the carbonyl carbon, they can be formed in either direction from amino or carboxyl polymers, and from amino or hydroxyl polymers, respectively.

Affinity and selectivity of the sorbent are largely determined by a combination of two or more different residues. The term "residue" means any distinct chemical moiety or a distinctly identifiable, usually repeatedly occurring, arrangement of chemical moieties of the same or different kind capable of assembling on the nanoscopic scale (by itself or part of itself or within a cluster of residues of the same or different kind) into a complex or a place of high and/or selective affinity toward at least one complementary structure or surface region of at least one protein or peptide, as long as the affinity is stronger than a mere van der Waals-contact with CH or $CH_2$ repeating units of the lattice or polymer chain on the sorbent surface. Such a place at the solid/liquid interface is, in analogy to the description of specific interactions involving biomacromolecules, called a "binding site". A residue can thereby be an entirely synthetic or a natural product or a fragment or combination thereof, but should be amenable to chemical synthesis and/or derivatisation. It may comprise more than one distinct chemical moiety (including chemically unreactive moieties such as, for example, alkyl or alkylene units which are nevertheless capable to engage in hydrophobic or dispersive interactions).

Since two or more different residues are introduced into the sorbent in variable ratios, a binding site will comprise two or more, identical and different residues. The totality of residues involved in the formation of a particular binding site is located in close two- or three-dimensional spatial proximity of each other and may, but does not necessarily have to, involve residues on neighbouring surface functional groups or neighbouring repeating units of a polymer film. Individual residues of a common binding site may as well belong to different strands of a crosslinked or surface-grafted polymer (the same principle applies to the counterparts of binding exposed on the respective protein or peptide surface). On the other hand, a particular residue can be shared by two or more adjacent or overlapping binding sites. Due to the random (statistical) nature of the distribution of crosslinkages and residues onto the functional groups on the surface or within a polymer film, a resulting distribution of similar, but neither structurally nor energetically identical binding sites can be formed. As a result, the sizes and affinities of these binding sites toward the target protein or peptide may differ to a considerable extent which has, however, in practice not proven as a disadvantage.

"Binding" between the binding sites of the sorbent and the target protein or peptide shall be reversible and shall therefore take place via any form of non-covalent interaction between complementary chemical moieties of the sorbent. Among the prevailing non-covalent modes of binding are ionic, hydrogen bonding, donor-acceptor charge transfer, $\pi$-$\pi$, cation-$\pi$, dipole, coordinative, dispersive, and hydrophobic interactions, but often mixed and non-stoichiometric forms are encountered which do not allow to specify the individual binding mode contributions. Thus, single, double or multiple simultaneous contacts may occur between the binding partners which may involve the same or different residues. Physical and entropic forces influencing the mobility of an analyte on rough surfaces and in microscopic pores as well as solvent-mediated interactions may add to the factors responsible for binding. In certain instances, the resulting complex comprising the sorbent and at least one bound protein or peptide may be detectable or even isolable, but more often it will be of transient character only. There is also no useful lower limit imposed on the binding strength since such values would not only be an intrinsic property of a given sorbent-analyte pair but also strongly solvent-dependent. Moreover, even differential Gibbs enthalpies as small as 1 kcal mole$^{-1}$ can be still resolved by chromatographic methods due to multiple serial equilibrations in columns whose theoretical plate numbers can adopt values of about $10^3$ to $10^4$ per meter of chromatographic bed length. In chromatographic applications, binding should also not be too strong, because otherwise reversibility would be difficult to achieve under ambient or biocompatible conditions.

As the sorbents of the present invention are concerned, a residue may be connected to a functional group on the surface of a solid support material, including an optional polymer film covering said surface, and, if so, comprises the entire partial structure pointing away from the surface from the point of attachment at the functional group, or at least that part of it which occurs in an identical manner on different functional groups. Not necessarily has the entire residue to engage directly in the binding of the target protein or peptide. The residue may as well contain such atoms or moieties which only have the purpose of separating or connecting the actually binding structures from/with each other or to provide a geometrically suitable framework for the binding site in order to present the binding structures to the target. Optional spacer, branching or other linker units between the functional groups on the solid support material, especially on an optional polymer film on its surface, and the actually binding structures are thus formally assigned to be part of each residue to which they make at least one connection. The connection can usually be achieved via at least one special derivatisation process of the functional groups, in a stochastic (ubiquitous) or selective manner, prior or subsequent to the application of an optional polymer film onto the carrier medium, in a homogeneous or heterogeneous fashion. Accordingly, a solution or thin film of the polymer may be reacted with pre-synthesised derivatisation reagents, which already contain the residues or precursors thereof.

However, if the functional groups, or structural parts of them, are converted by derivatisation with residues or precursors thereof into moieties of a different kind, or are then forming an integral chemical unit with additional atoms of said residue (e.g., the nitrogen atom in the conversion of an —NH$_2$ functional group into a —NHCO—R residue), they may as well be regarded as having basically lost their character as functional groups and instead be regarded as a structural moiety belonging to said residue.

If residues of the same or different kind are attached individually to functional groups of the solid support material either directly or via a covalent, conformationally flexible linker, it is assumed that they adapt to their complementary counterparts on the target protein or peptide surface independently, the driving force being the minimisation of the overall Gibbs enthalpy. It is therefore not necessary for the purpose of the present invention that the residues of the binding site are organised in the correct three-dimensional orientation for optimum binding of a given protein or peptide epitope (as for example in a natural antibody); they only need to be able to assume such an orientation through exploration of their conformational space (substrate-induced fit). In many cases, especially if differential binding is strived for, two or more, different or overlapping epitopes of the target protein or peptide may be recognised by the same sorbent.

While the term "residue", which refers to the overall unit which is pointing away from the sorbent surface and repeated many times identically or similarly thereon with the intent to engage in analyte binding, is as such functionally defined, such a residue may consist on the molecular-structural level of one or more distinguishable, but within themselves contiguous subunits, into which it may—just formally—be fragmented, so-called "structures". This term is being used throughout the invention in its broadest possible meaning. Although somewhat arbitrary, the division of a residue into different structures should follow the principle of chemical likeness and intuition, whereby molecular moieties or fragments should be meaningfully grouped together according to common structural and/or physical properties. The functions associated with different structures belonging to the same residue may thereby likewise be different: some structures may be related to analyte binding while others are not. In view of myriads of possibilities of realising sorbents according to the invention due to small structural changes of the residues, on such a basis the essential parts of a residue can be separated from the non-essential parts. To those optional structures not primarily involved in analyte binding, "linkers" are belonging which are short molecular (often simple hydrocarbon) tethers, optionally comprising functionalities or unsaturated valencies at one or both ends for making the necessary connections, and forming the ties between the actually binding structures and adjacent structures and/or the sorbent surface. It would thus for example be possible to employ several different residues in a sorbent of the invention which all comprise a first residue comprising a pyridyl ring and a second residue comprising a carboxyl group but linkers of different kind, length, or connectivity and optional or missing further structures. Such a group of residues could then be distinguished on the molecular level but they would functionally altogether qualify as "first residues" and "second residues" within the meaning of the invention. The use of linkers will be discussed in more detail farther below.

The structures of the residues responsible for the target recognition involve "residues comprising a pyridyl ring, whose hydrogen atoms may be substituted" as a first residue, and "residues comprising a carboxyl group" as a second residue.

According to common nomenclature, "pyridyl" denotes a partial structure (radical) derived from any mononuclear 6-membered aromatic ring system consisting of five carbon atoms, one nitrogen atom and no other heteroatom (i.e., pyridine or aza-benzene) which is connected to the remainder of the residue by at least one single bond, although various substituted pyridines may also be known under different trivial names. Further aromatic, heteroaromatic, aliphatic or heteroaliphatic rings or ring systems may nevertheless be attached to the pyridyl ring as substituents via immediate single bond connections to at least one ring atom, optionally via spacer units. Extended ring fusion (two-point substituent attachment) is, however, only possible with aliphatic or heteroaliphatic rings, such that the pyridine n-electron system is not extended into the full length of the additional ring, and ring systems of higher nuclearity are avoided. Due to the multiple individual possibilities of fragmenting a residue into structures, it should be sufficient within the context used here if at least one viable first residue and second residue fragmentation leads to a pyridyl ring and a carboxyl group, respectively.

"Substituents" are organic radicals (except hydrogen) which are considered as optional parts of the pyridyl ring and are thus thought to engage also in analyte binding.

In the prior art, sorbents showing high affinities and selectivities are predominantly known from solid support materials to which antibodies or other high-molecular weight receptors of biological origin are affixed. Such antibodies first have to be raised specifically against the target antigen in a biological process involving living organisms, or the target protein or peptide must be reversibly conjugated to an antigen or to one component of only few previously known natural affinity pairs. The sorbents of the present invention can be distinguished from those by the fact that their residues are accessible by chemical synthesis, by a low molecular weight and high chemical stability. However, they may as well be implemented as stationary phases in all types of affinity chromatographic methods.

The terms "protein" and "peptide" represent poly- and oligoaminoacids, respectively, as chemically, biosynthetically or bioanalytically distinctly identifiable entities which can be of synthetic or biological origin (regardless of their possible occurrence in nature), of linear or branched, homo- or heteromeric sequences, and upon which no minimum or maximum sequence length or molecular weight limit is imposed. A minimum requirement is that they should be composed of at least two amino acids which are connected via at least one amide bond, which would, for example, correspond to a dipeptide. The presence of non-proteinogenic or completely unnatural amino acids, β-amino acids, N-alkyl amino acids, additional peptidomimetic units etc., which are all still capable of forming peptidic bonds, should not be detrimental. Small (oligo)peptides can often be prepared synthetically via stepwise or convergent methods; the term peptide shall in such case additionally encompass obtainable structures formed via unusual connectivities such as, for example, depsipeptides or peptoids. Larger proteins typically possess a defined three-dimensional structure which may adopt numerous of different shapes such as, for example, globular (albumin) or filamentous/fibrous (actin, collagen) shapes; they may be soluble in the cytosol, membrane-bound, part of the extracellular matrix, or can be presented on the surface of a cell. Due to the tiny amounts of proteins that can be handled with modern molecular biological methods, their primary amino acid sequence does not need to be known in order to identify them; sometimes it is not even known whether they are present as a homogeneous composition. Proteins or peptides bound to the surface of a (colloidally) dispersed carrier (nano)particle such as, for example, a virus, a quantum dot, or a latex sphere, are usually required to be cleaved off first in order to expose also the otherwise shielded parts of their entire molecular surface for interaction with the sorbent before they can be employed in the separation method of the invention.

The above terms include on the one hand non-covalent peptide aggregates as well as homo- and heteromultimeric proteins, but on the other hand also functional or non-functional subunits of a full protein such as the products of enzymatic digests or disulphide bond reductions, but also de-novo designed mini-proteins such as <<Affibodies™>>, <<Anticalins™>>, <<Nanobodies™>>, or other artificially reconstituted active sites. Metal ions or complexes may be contained in proteins, usually in their active sites. Analyte proteins can be modified by in-vivo posttranslational modifications, such as phosphorylation, sulphatisation, glycosylation, glucuronidation, or ubiquitinylation. Conjugation with glycosides and lipids results in glyco- and lipoproteins, respectively, consisting of additional structural units beyond just amino acids. Protein modifications whose up- or down-regulation can serve as markers for certain pathological states of the organism in which they are produced are thereby generally of utmost importance. Similarly, in-vitro biochemical modifications of a surface as well as an active or allosteric site of a protein include the formation of reversible or irreversible complexes with substrate agonists or antagonists as well as all kinds of protective group chemistry of amino, carboxyl, and side chain functions. Proteins or peptides can further be chemically or biochemically tagged (e.g. oligohistidine sequence-tags, conjugated dyes or radioactive labels) or fused with another (carrier) protein with the aim of enhanced expression, solubility, excretion, detection or separation of the protein or peptide, whereby the point of conjugation might be cleavable, but they can also lack part of their native sequence such as, for example, a membrane anchoring tail.

If one of the terms "target protein", "target peptide", or simply "target" is used, the particular protein or peptide, or multitude of proteins or peptides (usually related by structure, classification, synthesis, or origin), is meant for which the sorbent with its specific residues is designed. This is normally the analyte or component of the feed mixture showing the highest affinity for the sorbent. The target protein or peptide may be distinguished from its potential proteinacious side products not only by its amino acid sequence (down to single-point sequence mutations or deletions and including those resulting from alternative splicing or SNP variants during gene transcription) but by its full secondary and tertiary structure elements which include the presence of differently folded (native, unfolded or misfolded) states. The target protein or peptide often is, but does not necessarily need to be the main component of the feed mixture (by weight or molarity), not even the main peptidic component. Regardless of its abundance within the mixture, the target often is, but does not necessarily be a valuable mixture component or the particular substance required to be purified, while the latter may possibly be contained in the flow-through fraction. Since many proteins or peptides have demonstrable toxic properties, in health- or environment-oriented applications predominantly the target can also be such a toxic or otherwise unwanted properties exhibiting protein or peptide in a mixture from which it has to be depleted. It could also be that the target is not a major product but a minor side product of a manufacturing process which is required to be separated or removed from the remainder of the mixture, whereby the concentration or purity of another mixture component—usually the principal product—which itself may or may not be a protein or peptide, is increased. Pointing towards the multi-step blood plasma fractionation process, many consecutive fractionations may be necessary to rectify a whole bunch of different proteins or peptides being simultaneously present in the feed mixture, whereby the flow-through of a particular stage of fractionation may be adsorbed at the next stage, or vice versa.

The collectivity of all solutes within the mixture to be separated—including the target—which are capable of at least weak interactions with the sorbent of the invention under suitable conditions is termed as "analytes". Most analytes will be proteins or peptides, because these are the analytes the sorbent is designed for, but under certain circumstances it is possible that small, non-peptidic molecules may belong to this group. Closely related analytes may form together a synthetic or biosynthetic library, for example one derived from a tryptic digest, a phage display library or an expression product of a randomised cDNA library which has been appropriately transcribed in vivo or in vitro. The affinity of the sorbent, however, usually drops rapidly for analytes having structures deviating from the target group, and approaches zero if they are structurally unrelated to the target(s).

Preferred proteins or peptides will have an isoelectric point pI of from 4.5 to 8.5 and their molecular weight can range from 100 to 500,000 Da. These pI values will approximately match the acidity $pK_a$ of the pyridyl ring incorporated in at least one of the first residues. The particularly preferred target proteins of the sorbent of the invention are "antibodies" or mixtures thereof, a term which shall also include fragments (light and heavy chains, Fab and Fc regions, Sc variable regions, etc.) of antibodies, artificial molecular constructs from such fragments (diabodies, triabodies), oligomeric associates of antibodies, as well as antibody- or antibody fragment-containing fusion proteins, or other types of conjugates such as those containing detectable tags like glutathione or GFP which may also be chemically linked with each other. It may be a polyclonal or a monoclonal antibody. Among the immunoglobulins (Ig, γ-globulin) in general, the antibody may belong to any of the isotypes IgA, IgD, IgE, IgG, or IgM, each of which can in turn be divided into several subclasses. The antibody can be of human or other mammalian (typical: murine or rodent (mouse, rat, rabbit, hamster, guinea pig), goat, sheep, dog, pig, bovine, horse) origin. The preferred antibodies are human or humanised (chimeric) antibodies. Their idiotypes can be directed against all types of antigens (other antibodies or biological substances, small molecules).

A "mixture containing a protein or peptide" means a mixture that can be of various origin. There is no severe limitation of the present invention as to the source from which the mixture has been obtained. The only requirement is that it contains at least one protein or peptide which would qualify as an analyte for which the sorbent of the present invention exhibits at least weak receptor properties. The mixture may thereby contain two or more different proteins or peptides which are either intended to be separated collectively from the remainder of the mixture (i.e., all of them are separation targets) or to be separated from each other (i.e., only one or a few of them are separation targets). The structural motifs (epitopes) of the at least two proteins or peptides within the mixture which are recognised by the residues of the sorbent may both be identical, similar or partially identical, or different. It is assumed that the latter cases will lead in many instances to different types of interaction with the sorbent, and thus to larger differences in binding strength, provided that the at least two proteins or peptides are of comparable molecular weight and contain about the same number of recognisable epitopes.

If the protein or peptide is a naturally occurring or recombinantly produced substance, it may be obtained from fresh or dry extracts of liquid or solid biological material such as animals, plants, microbes, or viruses (including breeded or transgenic species which overproduce the product), extracts from cell cultures or cell culture media, microbial (bacterial or fungal) or enzymatic fermentation broths, commercial feedstocks, or any combination thereof. Alternatively, the mixture containing the protein or peptide can be the raw product of a chemical synthesis or partial synthesis. This especially includes standard solution and solid-phase peptide synthetic methods, performed either manually or in an automated fashion.

As typical for any purification technique and especially any chromatographic technique, the exact conditions to be used are not only dependent on the constitution of the target protein or peptide but on that of the sample matrix as well. The "matrix" is a term in use for the collectivity of all active and non-active constituents of the mixture, with the exception of the target(s) but including the medium in which they are dissipated. This is because not the absolute physical or chemical properties of the target protein or peptide are commonly utilised in a separation process but rather the differences of said properties between the target protein or peptide and all or a few specific matrix components. Usually, the composition of the matrix is at most only partially known (both qualitatively and quantitatively) since one single analysis method is often not able to detect all constituents, at least not with equal sensitivity. Intermediate products obtained at different process stages during the downstream isolation and purification of a chemical or biological material represent different matrices within the meaning used in the context of the present invention. The entire mixture (target and matrix combined) to be tested for its adsorption behaviour on the sorbent is in an analytical context often also termed the "sample".

Prior to treatment with the sorbent of the invention, raw chemical or biological materials can be partially purified via further pre-processing by any combination of further non-destructive unit operations, in particular traditional separation processes which may comprise filtration (including micro- or ultrafiltration), dialysis and electrodialysis, washing, precipitation, centrifugation, ion exchange, gel filtration, dissolution, evaporation, crystallisation, drying, grinding, any way of viral reduction treatment, and also conventional chromatography (either chromatography on sorbents of low specificity or conventional affinity chromatography with biological residues) in order to remove as much waste material as feasible (e.g., insoluble matter and the majority of proteins, nucleic acids, carbohydrates, lipids, and inorganics in case of biological material, leaving only the valuable substances), harmful or aggressive substances or those substances which are suspected to possibly deteriorate the sorbent or diminish its separation ability, from the chemical or biological material, thereby increasing the concentration of the target prior to contacting it with the sorbent. Within this context, LC/LC-coupling techniques are referenced to. Dry mixtures such as freeze-dried or lyophilised material need to be taken up in a suitable feed solvent before they are treated with the sorbent. It is desirable that the dissolved mixture is homogeneous and free of suspended or colloidal particles. Similarly, the separation method of the invention can also be combined subsequently with one or more steps of the kind given above.

Many proteins or peptides are already manufactured on an industrial scale and have found applications in medicine, nutrition (e.g. dietary supplements), cosmetics, or agriculture. A large-scale production of most of them can until now economically and within a reasonable timeframe only be achieved by extraction of biomass, i.e. biological material obtained for example from medicinal plants, microbial fermentations using prokaryotic or eukaryotic microorganisms, or cell cultures of higher organisms up to insect or mammalian cells (e.g. the frequently used CHO, NSO, BHK, or the immortalized HeLa cells). In summary, frequent sources of mixtures according to the invention are therefore biosynthetic products, such as those obtained from a microorganism or a cell culture, or from a crop extract.

Microbial fermentations include submerged or floating cultures of bacterial or fungal (e.g. yeast) strains. Products can be extracted from whole organism harvests or from separated parts such as the mycelium and/or the corresponding culture medium supernatant into which they may be secreted. Semi-synthetic procedures include both downstream chemical modifications of natural products or intermediates and the biotransformation of synthetic feedstocks. In all cases, side products often comprise protein isoforms, truncated forms and accumulated intermediates or follow-up products along the biosynthetic pathways leading to the targeted protein or peptide. These may additionally be accompanied by ubiquitously secreted antibiotics, endotoxins, mycotoxins, pyrogens, promoters or inhibitors of cell proliferation, protease inhibitors, defoaming agents, residuals of incompletely digested nutrients, products of partial degradation, as well as high-molecular weight and partially insoluble components (e.g. cell debris) as they may result from final-stage cell lysis of the producing organism. Cell lysates often further increase the complexity of the mixture due to the release of additional substance classes like nucleic acids and a vast number of so-called host cell proteins into the extractable medium.

The term "separation" with relevance for the separation method of the invention includes all kinds of segregating or splitting a mixture into its parts, particularly dividing one or more structurally different components, which are molecularly dissolved in a liquid, and spreading them into different liquid fractions. One outstanding component of the mixture is always the target protein or peptide which should experience a separation from at least one other mixture component. It thereby does not matter whether the target is separated in one fraction and the collectivity of side products separated in one other (common) fraction, or if each individual mixture component is separated in its own fraction from any other component, or if the method results in anything located in between these extremes. It is sufficient if in at least one liquid fraction obtained after performing the method an enrichment of at least one dissolved protein or peptide already present in the original (feed) mixture is observed. Separated side products do not necessarily need to be recovered as separate liquid fractions; they may also stay bound to the sorbent for being discarded as such, for example. It would not be unusual if the separation process remains incomplete which would turn into yield losses in the fractions containing the desired product of value. Sharp fractionation which avoids overlapping elution bands would increase the quality of separation (i.e. purity) at the cost of further yield losses.

The terms "concentration" and "purity" relate to the given or achievable fractional content of the respective substance in the mixture, whereby the term concentration is referring to solutions with inclusion of the amount of solvent in the total reference amount of mixture, whereas the term purity refers to (sometimes hypothetical) dry mixtures without giving consideration to solvents (including residual water). Most often they are stated as either weight or molar fractions (weight/weight, weight/volume, moles/moles, moles/volume). A higher purity can thus be attained at the cost of a higher dilution (i.e. lower concentration) or vice versa, depending on the more important end to be achieved in a particular system. The measure for determining the actual values of these indicators as used herein is by HPLC peak area, whereby it has to be noted that every quantification method except for weight shows a certain bias for well-detectable mixture components versus badly-detectable mixture components, and may also yield non-linear calibration curves. Insoluble material, for example, is not quantifiable by HPLC. Depending on its origin, the way of its isolation and pre-processing, the mixture may typically contain the targeted protein(s) or peptide(s) in a (combined) purity of from 1% to 99%, preferably of at least 10%, more preferably of at least 50%, the remainder being side products or compounds which are structurally and functionally unrelated to the target such as residual solvents, reagents etc. Depending on the actual purification task, the separation method of the invention can therefore be used both as an initial capturing or isolation step out of very dilute or crude mixtures, or as a final polishing step of an already pre-purified mixture containing an almost pure target protein or peptide. The number of side products and other constituents of the mixture may range from one (e.g. a single-point sequence mutation or deletion) to an essentially infinite number (e.g. untreated physiological samples). The kind of side products is as well dependent on the source of the raw material and prior processing.

The term "contacting" refers to any appropriate treatment of the initial (feed) mixture being present in a liquid (mobile) phase with the sorbent as the solid (stationary) phase by establishing physical contact between the phases both on the phenomenological (wetting) as well as on the molecular (surface or pore diffusion) scale. Contacts formed should be intense enough to enable possibly all molecularly dissipated components of the mixture, but at least the target protein or peptide, to reach all external and optional internal sorbent surfaces where residues are located and then to interact with them. Contact formation can occur under static or (plug, laminar, turbulent etc.) flow conditions, e.g. over a fixed or fluidised (expanded) bed of sorbent particles. Since the mixture will be dissolved in a first liquid (feed liquid or adsorption liquid), this will be a heterogeneous process and contact formation may macroscopically be accelerated via stirring or shaking of the resulting suspension, although there is no time limit for terminating this operational step unless the establishment of a steady-state binding equilibrium of the target protein or peptide and optionally of the side products to the sorbent would be approaching.

As used herein, the term "liquid" refers to any solvent (including water as the most important one) or mixture of solvents which possess at least weak solubilising properties for one or more components of the mixture to be separated. Liquids of different composition may be employed for treatment of the sorbent in the different steps of the method, since in each step the respective liquid employed therein has to fulfil a particular task which it should enable, such as target adsorption (binding), target desorption (release), or sorbent cleaning. Within a chromatographic environment, a liquid which enables a dynamic equilibrium exchange of one or more components of the mixture with the sorbent is often also termed as a mobile phase. Since chromatographic separations on the sorbent of the present invention are predominantly dependent on both strongly polar and hydrophobic interactions, a broad variety of liquid compositions having differentiating solvation capabilities for individual mixture components can be used, depending on which type of interaction should be favoured. To further modulate the strength of any or all of these interactions over the time course of any given step of the separation method, it may sometimes also be advisable to gradually change the composition of the liquid used within said step, e.g. via gradient mixing. Therefore, the composition of a liquid dedicated to fulfil a specified task does not need to be constant over the full time lapse of the process step in which it is employed. The specific solubility of the target protein or peptide has also to be taken into account when choosing suitable adsorption and elution liquids. Proteins, except for those which are membrane-bound, normally require the use of liquids of high aqueous content, if they have to be conserved in their native states and aggregation has to be prevented. Many proteins or peptides tolerate also low to moderate percentages of dimethyl sulphoxide, dimethyl formamide, acetonitrile, or the lower alcohols and glycols. Since the sorbents of the invention are chemically resistant to almost all protic and aprotic organic solvents, especially if the bulk solid support material contained in the carrier is shielded by a surface polymer film being the only material in direct contact with the liquids, preference is further given to those predominantly polar liquids which facilitate swelling of the sorbent or at least said optional polymer film located thereon. The exact polarity of a compatible liquid mixture can thereby be easily fine-tuned by way of its composition.

Furthermore, to such liquids or liquid mixtures small amounts of auxiliary substances such as—preferably volatile—acids, bases, or buffers may favourably be added, thus enabling to switch between different solvation capabilities via adjustment of the pH of the applied liquid (or, in partially organic eluents, the apparent pH) and thereby the degree of protonation and/or deprotonation of selected or all analytes and/or of selected or all residues of the sorbent. Useful substances in this respect are, for example, formic acid, acetic acid, trifluoroacetic acid, and their salts. The addition of high concentrations of inert, organic or inorganic salts can also be useful to modify the ionic strength of a liquid and thus to selectively break ion pairs between analytes and the sorbent via competitive interactions. However, in preparative applications such non-volatile salt additives are difficult to remove later on from the recovered eluate if the target protein or peptide is intended to be further purified by crystallisation.

It may under certain circumstances be advantageous to use further organic modifiers together with the sorbent in the resolution of protein or peptide mixtures, which are acting by a mechanism reaching beyond a pure adjustment of liquid pH or ionic strength. As "modifiers" small molecules or macromolecules or mixtures thereof are summed up which are not liquids with solvating properties by themselves but which may be dissolved or suspended in small amounts in one or more of the various liquids employed in the separation method of the invention either to help or prevent the solubilisation/elution of certain components of the mixture to be separated during the particular step of the method, or for a number of secondary (technological) reasons, such as, for example, long-term stabilisation and storage of solvents, prevention of sorbent biofouling, preservation of analytes from chemical or biological degradation or from coagulation, enhanced solvent miscibility, sorbent swelling, improved analyte detection, breaking of water structure, controlled protein unfolding or refolding etc., depending on the individual separation problem. Special examples of organic modifiers are ion-pairing reagents, surfactants (detergents) and chaotropic reagents.

"Rinsing", "washing", and "regenerating" are different expressions used for better distinguishing the stepwise treatment of the same sorbent with different kinds of liquids. The liquids are thereby rather differentiated by the tasks they perform than by their composition. The actual procedure of treatment may thereby be very similar and sometimes only differs by the decision to be made whether the liquid has to be further refined, fractionated, recollected, or discarded based on the substances dissolved therein after the treatment. Rinsing is directed to a treatment with a liquid that ideally solubilises and releases from the sorbent any mixture component except for the target which may have been unspecifically bound by the sorbent. Washing is directed to a treatment that is intended to solubilise and release from the sorbent all residually bound mixture components, even those which may be stronger binding than the target. Regenerating is directed to the use of liquids which are capable to remove traces of the washing liquid and to restore the ideal physical and chemical properties of the clean sorbent for use in the adsorption step at the beginning of the next run of the method.

"Immobilisation" means a process of eliminating or substantially retarding the long-range lateral and/or vertical mobility of a protein or peptide on the surface of a sorbent which may otherwise be caused by either statistical, diffusional migration (Brown's motion) or directed physical or chemical forces (e.g. osmotic pressure, shear flow). The macroscopic two- or three-dimensional position of an immobilised protein or peptide on the adsorptive part of a surface can therefore be regarded as being fixed on a short time scale. Inevitable small fluctuations in the order of nanometers around the centre of immobilisation such as conformational changes, molecular rotations or oscillations, hopping between adjacent binding sites, or any translational motion within the combined radii of the protein or peptide itself and the residue to which it is bound as well as an (optionally polymeric) tether applied for fixation of the respective binding site residue to the surface, still remain unaffected. Slow release of the bound protein or peptide by crossing the binding surface layer on a large time scale may as well be a desired property.

In a central embodiment defining a composition of matter, the present invention is directed toward the target-specific design of a novel sorbent. Solid support materials having functional groups have been used for subsequent surface derivatisation, yielding a two- or three-dimensional arrangement of multiple residues suitable for multivalent and/or multifunctional spatial interaction with the target protein or peptide included therein.

A general aspect of the invention can therefore be described with a sorbent comprising a solid support material, the surface of which comprises first residues comprising a pyridyl ring, whose hydrogen atoms may be substituted, and second residues comprising a carboxylic group.

More specific aspects of the invention may be described with sorbents according to the first, second, third, and fourth aspect as specified in the section "Brief Summary of the Invention".

The term "wherein none of said functional groups comprises both said first residue and said second residue" as used for the description of the sorbents according to the third and fifth aspect means that less than 5% of the available functional groups of the surface of the carrier, preferably less than 1%, more preferred less than 0.1%, still more preferred none of the functional groups, carry both a first and a second residue.

In a specific embodiment, it is not detectable by common analytical methods such as spectroscopic methods that a functional group carries a first and a second residue.

Said solid support material of the sorbent can be chosen from the group comprising polystyrene, polystyrene sulphonic acid, polyacrylates, polymethacrylates, polyvinyl alcohol, silica, glass, starch, cellulose, agarose, sepharose, and dextran, or any composites thereof. The solid support material may belong to the class of generic bulk or further surface-modified materials, e.g. to introduce surface functional groups or to increase aqueous wettability.

In a special embodiment, the sorbent may also comprise an easily detectable tag, such as an optically absorbing, an optically emitting, a radioactive, or a mass- or radiofrequency-encoding tag. The tag may be used to identify a particular sorbent with its individual combination of residues even in sorbent mixtures or to facilitate the detection of protein or peptide binding. The tag can be incorporated into the core of the solid support material, or alternatively together with the residues onto its surface.

To the residues comprising a pyridyl ring, as they were mentioned above, especially belong some which are frequently occurring in chemical structures of small organic molecules, such as those of the list depicted in FIG. 3. Fine-tuning of the specific affinity of the sorbent for a given particular protein or peptide is attained via careful selection of the respective substituents on the pyridyl ring, the molar ratio of first and second residues, and the introduction of optional further residues. Therefore it will become clear that the full variability cannot be exhaustively dealt with; instead the conceptual framework for building up a sorbent according to the existing demands will be given.

For simplicity, only one mesomeric formula is shown for each structure in FIG. 3. Moreover, for the purpose of the present invention it is sufficient within the meaning of the term "pyridyl ring" if at least one reasonable mesomeric or tautomeric formula of heteroaromatic pyridine character of such a structure exists even if there are additional non-heteroaromatic formulae possible. The connection between the ring system and the remainder of the residue, and thus eventually the solid support material, can be made via any of the ring atoms, including free valencies at the heteroatoms, as attachment points.

Pyridyl rings and carboxyl groups are both ionogenic which means that an electronically neutral atom or any group containing it can, under the conditions of the separation to be performed (i.e., usually mild or ambient conditions that do not affect the structural integrity of sorbent or analytes), be reversibly converted, (e.g. by protonation or deprotonation) into a cation or anion which is either stable under ambient conditions or in equilibrium with the uncharged form. More specifically, the first residues of the sorbent will, at least in part, be amenable to protonation and thus, at least in part, be present in their protonated form. Although the charged forms are not explicitly shown in the figures, the equilibrium can actually reside almost entirely on either side under the given conditions, and there can still be a measurable mutual interconversion between the charged and the uncharged form. Protonation depends on the environmental pH but is also prevalent in most aprotic organic solvents and makes it difficult to distinguish whether both forms or only one of them is responsible for the affinity exhibited by the sorbent. The exact degree of protonation of each residue will depend on its basicity, the concentration and kind of acid present, on the mobile phase used and on the way of pre-conditioning of the sorbent.

Depending on the particular separation task, it may thus be advantageous to either treat the mixture to be separated with a sorbent which exhibits residues which have been conditioned to be predominantly in the uncharged state or predominantly in the charged state, or which may even change the state of charge one or more times during the separation (e.g. by buffer exchange as known from weak ion exchangers). Conditions under which ionogenic pyridyl rings and/or carboxyl groups of the sorbent are partially ionised are also possible, as can easily be imagined if a separation is performed in an environment whose pH approaches the pK value of the respective structure. It might also be necessary to manufacture or store the sorbent in an uncharged state while performing the separation in a charged state, or vice versa.

A pre-conditioning of the sorbent involving an aqueous buffer system of a pH of about 5 is preferred, especially if further (third) residues comprising an amine structure (see below) are present. Such treatment will establish a uniform distribution of counterions belonging to each sort of ammonium structure or other ionogenic residue. The strength of hydrogen bonding exhibited by the residues towards an analyte is also influenced by the nature of the counterions which are expected to stay within the surrounding solvate shell and to form ion pairs with protonated residues, their basicity and/or their <<hard>> vs. <<soft>> polarisability behaviour.

Further substituents can be bound to the pyridyl ring, and can be chosen for each ring independently. As shown in FIG. 3 for exemplary structures, the substituents $R^1$, $R^{1'}$ . . . $R^4$ independently represent hydrogen (H), an organic radical. Without wishing to be confined to a particular ring geometry or substitution pattern, suitable substituents may especially comprise those which are composed of one or more of the following simple organic radicals: $C_1$-$C_{20}$ linear or branched alkyl, alkenyl, alkinyl, cycloalkyl, cycloalkenyl, aryl, arylalkyl, arylalkenyl, arylalkinyl, alkyloxy, alkenyloxy, alkinyloxy, cycloalkyloxy, aryloxy, arylalkyloxy, alkylthiyl, alkenylthiyl, alkinylthiyl, cycloalkylthiyl, arylthiyl, arylalkylthiyl, halogenalkyl, halogenalkenyl, halogenalkinyl, halogencycloalkyl, halogenaryl, halogenarylalkyl, halogenalkyloxy, halogenaryloxy, halogenarylalkyloxy, halogenalkylthiyl, halogenarylthiyl, or halogenarylalkylthiyl.

The fully synthetic sorbents of the present invention have to be distinguished further from conventional affinity media in which the surface-bound residues are themselves often proteins or peptides or parts thereof and which closely mimic known biological ligand-receptor interactions. In general, such media suffer from the disadvantages stated in the beginning.

Degrees of derivatisation with each residue are preferred in which the first and second residues will be present in a molar ratio of about 3:2, in a broader sense at least of from 1:1 to 2:1. The sum of the degrees of derivatisation for first and second residues combined is preferably kept close to at least 50% (based on the number of functional groups available for derivatisation) in order to promote the formation of multivalent interaction sites of mixed composition while still keeping the binding capacity of the sorbent for the target protein or peptide high. First and second residues may then be present, for example, at degrees of derivatisation of close to 35% and 25%, respectively. Preferred third residues (see below) comprise amine or amide, more preferably primary amine structures. In such case, the first, second, and third residues are present in a molar ratio of about 3:2:3, respectively. Relative deviations of ca. 10% around these values are tolerable.

In one embodiment, from 5 to 95% of the functional groups are linked to the interacting structures of said first and second residues (pyridyl rings and carboxyl groups, respectively), preferably from 20 to 90%, more preferred from 30 to 80%, still more preferred from 40 to 70%, further preferred from 50 to 60%. Since the ratio of first to second residues may be freely selected, it is possible to optimally adjust within said given ranges a sorbent to a specific separation problem, e.g. the separation of a protein or peptide from a mixture comprising said peptide or protein, or to adjust the sorbent to the optimal increase of the concentration and/or purity of a peptide or protein from a mixture comprising said peptide or protein. This variability renders particularly useful the sorbent or the sorbents according to the invention for the mentioned separation or increase and/or purity problems.

Accordingly, in one embodiment, from 5 to 95% of the functional groups are linked to the interacting structures of said first and second residues (pyridyl rings and carboxyl groups, respectively), preferably from 20 to 90%, more preferred from 30 to 80%, still more preferred from 40 to 70%, further preferred from 50 to 60%; wherein the first and second residues are present in a molar ratio of from 1:1 to 2:1.

The type of residue attachment can be any variant of a covalent bond (homo- or heteroatomic, variable bond order) and may either be made directly with functional groups on the surface of the solid support material or on an optional polymer film covering said surface, whether attached to its backbone or to its pendant linear or branched side chains or optionally coupled via the termini of bifunctional linkers. In addition to the pyridyl rings which are the designated parts of the first residues to interact selectively with the target protein or peptide, these residues may thus also comprise covalent linkers. Such bifunctional linkers are intentionally not shown in the figures due to their large possible variability in length and chemical composition but they are known from standard solid phase synthesis or bioconjugation methods (e.g. succinyl); the most simple bifunctional linker would be an alkylene chain of a predetermined number of from 1 to about 20 atoms. Best suited linkers are conformationally flexible ones. The preferred covalent linkages which connect the entire residues to a polymer film will again be made of amide, urethane, urea, or secondary/tertiary amine bonds.

Within this context, it has to be mentioned that especially long alkylene chains or polyethylene glycol moieties used as linkers could exert additional, largely unspecific hydrophobic forces on said proteins or peptides in superposition or amplification of the primary effect of the first, respectively the second residue. Previously described linkers containing sulphur, however, which are easily synthesised and connected to activated surfaces, are not within the focus of the present invention since it is well known that sulphur atoms or sulphur-containing groups interact well with corresponding groups of the same kind on the molecular surface of an analyte, a fact that may be able to introduce special selectivities on its own which could possibly interfere with the binding mechanism of the sorbents presented here.

It can therefore not be excluded that possible additional chemical structures formed between such an optional linker and the functional groups of the solid support material and/or the interacting structures of the residues by way of their attachment are also accessible to various analytes and may thus aid in the selective retention of the target protein or peptide. The only practical limitations with regard to the chemical composition of the additional structural entities placed between the heteroaromatic structure as part of the respective residue and the surface of the solid support material are imposed by the requirement of chemical stability and compatibility with the conditions applied during the manufacture, storage, and use of the sorbent. Therefore it is also possible that the respective residue is incorporated via a specified attachment point as a sub-structure into a scaffold of higher complexity (including polymers) which may comprise additional residues of the same and/or different kind.

The residues can be coupled directly to the surface of a bulk solid support material, in particular by forming covalent bonds with functional groups on said surface. For example, the method of choice for coupling residues to the surface silanol groups of silica is performed with the help of chlorosilane- or alkoxysilane-terminated linkers whereas coupling to the hydroxyl groups of carbohydrate supports can be achieved through a variety of methods such as the classic cyanogen bromide activation. These methods are sufficiently known to those skilled in the art.

In a preferred embodiment, however, the bulk solid support material represents only a carrier the immediate surface of which is covered with a film of a polymer having functional groups, which are in turn at least partially substituted by pendant first and second and optionally further residues. Thus a thin interlayer is formed which moves the macroscopic shape-defining and the analyte-interacting parts of the sorbent apart from each other but does not significantly change the overall underlying surface topology and is therefore being considered as a part of that surface. The residues can be attached to said polymer functional groups which will turn the employed base polymer into an at least partially derivatised co-polymer. Suitable base polymers having functional groups are for example polyvinyl alcohol, polyvinylamine, polyallylamine, polyethylene imine, polyacrylic acid, polymethacrylic acid, and any copolymer or polymer blend comprising at least one of these polymers. Especially if the solid support material consists of a bulk polymeric material as a carrier whose surface is further covered with a film of a polymer, but also if non-polymeric carriers are used, the material the carrier is made of can be different from the material the film of a polymer is made of. Such difference can manifest itself for example in a different monomer composition, polymerisation regio- or stereochemistry, stereoregularity (tacticity), molecular weight distribution, degree of crosslinking, or combinations thereof.

The exact thickness of the polymer film and also the separation kinetics and capacity of the sorbent are thereby dependent on the state of swelling of the polymer, which itself will always be a function of the mobile phase composition, and can thus vary under different external conditions. For separations of proteins and peptides carried out in aqueous or mixed aqueous-organic media, it is preferable if the polymer is swellable in such media. This is accomplished most easily if the polymer is a synthetic polyelectrolyte. As explained above, the charge character of any possible ionogenic residues also influences the swellability of the polymer film to a certain degree which is again solvent-dependent. The term "aqueous" is used herein to describe liquids which contain more than 50% by volume of water, the remainder being other water-miscible solvents or additives such as inorganic or organic buffers, salts etc.

Such a morphology is designed to maintain unusually high mass transfer rates between mobile and stationary phases via pore diffusion. The linear or branched polymer itself has to be durably fixed to the surface of the rigid and firm carrier in order for the polymer film to withstand the conditions of the separation process for which it is made and stay in position throughout the entire process. The fixation can either be performed by internal crosslinkage of the individual polymer strands resulting in the formation of a continuous polymer network, or by grafting of individual polymer strands at one or more positions along the chain to the carrier solid. Crosslinkage as well as grafting can easily be achieved between the same or different functional groups of the polymer, or between the functional groups present anywhere in the polymer and those present on the surface of the uncoated carrier, respectively. The preferred crosslinking or grafting connections of the polymer will be made of amide, urethane, urea, or secondary/tertiary amine bonds. The terminal functional groups of the individual polymer strands are best used for grafting, which will result in an end-on configuration giving the highest chain flexibility.

Though a combination of both techniques would certainly be feasible, usually one of them is sufficient. The preferred way of fixation is crosslinkage (without grafting). The polymer chains may thereby be covalently crosslinked with each other to an extent of from 1% to 20% based on the number of functional groups available for crosslinking.

Additional supplementary residues could thus in principle result from the introduction of crosslinks into the polymer film if the crosslinking reagents contain chemical structures that are suited to interact with one or more analytes. Since the degree of crosslinking of the polymer is preferably held at a comparably low percentage, their contributions are believed to be rather negligible. The same is thought to be true for the contribution of additional amide (e.g. formamide) or urethane groups which may be remaining in a variable amount, but usually less than 1%, as a result from the synthesis of polymer films containing amino functional groups via incomplete hydrolysis reactions, resulting in statistical amine/amide or amine/urethane copolymers.

It is nevertheless possible to derivatise a solid support material with two or more different first residues and/or two or more different second residues, according to the definition of their respective partial structures. These may then differ from each other in their interacting structures (substituted pyridyl rings and/or carboxyl groups) or in their ways of linking these structures to the surface of the solid support material, or both. In a preferred embodiment, the total number of first residues and total number of second residues (or their degree of derivatisation equivalents, respectively) will be within the same order of magnitude in order to realise the maximum number of mixed-composition binding sites comprising all different first and second residues under the provision of a random (statistical) spatial residue distribution.

Usually and in a preferred embodiment, the first and second residues are not connected directly with each other but are separately attached to either a bulk solid support material itself or a polymer film supported by it as a carrier. Accordingly, the pyridyl ring and the carboxyl group are not linked to the surface of the support material via the one and same functional group.

On the other hand, two or more residues of the same or different kind can also be connected directly with each other through covalent bonds not involving the backbone of a polymer film or in any other way the surface of the solid support material. In such case, the boundaries between the individual residues begin to blur and are becoming arbitrary since they may only be left meaningful if the derivatisation history of the sorbent (i.e., the sequence and kind of derivatisation steps) is known. As is exemplarily shown in the schematic representations A-H of FIG. 1, two pendant functional groups on the surface of the solid support material can be derivatised with two different residues in many different ways (the long horizontal wiggly line here denotes a part of the surface which may itself contain further residues).

In addition to the case mentioned above of an equal distribution wherein each individual functional group carries one residue (in formulae A or B), they can also, for example, be aligned sequentially "in a row" (in formulae C, D) or in parallel (in formulae E, G) onto the same functional group. Such configurations can experimentally be achieved, inter alia, in that a residue contains itself a functional group which is the same as the polymer or surface functional group or different therefrom, and which may, after derivatisation of the polymer or surface functional group with said first residue, be derivatised itself (optionally after deprotection and/or activation) with the second residue (case C), or in that one functional group is derivatised at least twofold (in a single step or in a number of consecutive steps, such that a common functional group (case G) or a linker having a branched structure (case E) is shared by both residues (an appropriate example would be a two- or threefold alkylation of a primary amino group to yield a tertiary amino or quaternary ammonium moiety). The resulting configurations C, D, E, F could, however, also be achieved via an alternate path in which the surface or the polymer having functional groups is derivatised with a single derivatisation reagent already carrying both first and second residues in the correct mutual arrangement. More complex mutual arrangements of both residues such as macro- or polycyclic ring systems (cases F and H) are also imaginable, of course. In all cases except for A and B, the first portion of functional groups which is derivatised with the first residue always equals the second (same) portion of functional groups which is derivatised with the second residue.

All situations described above can under a unified view also be regarded as borderline cases of a more general situation in which the individual residues are arranged in a hierarchical order.

If one of the given examples is re-examined in view of this general representation, such a configuration can, inter alia, be realised in that the two different structures share a common linker or a part thereof through which they are attached to the surface of the solid support material itself. The two structures can thereby be arranged linearly on the same branch or on different branches, if the linker has a branched structure. The entire residue, i.e. the largest possible, uniform structural unit (including a possible linker terminating in the surface functional groups and all other substructures connected therewith), would then—just formally—be attributed to the first residue, while the second residue would—formally, again—in such a configuration only comprise the respective carboxyl group structure and possibly its immediate connective elements with the remainder of the overall (first) residue.

It has now surprisingly been found that any sorbent possessing a combination of the two structural features described above allows the easy recovery of a number of proteins or peptides, in certain instances with a purity higher than 98%, or with a final concentration of each impurity below 1% in a single step starting from only partially purified mixtures. Pharmaceutical grades can thus be obtained without laborious or cumbersome procedures. The concentration of proteins or peptides in crude materials such as those directly resulting from manufacturing on the industrial scale, can be enriched to high levels in a single step, too. Applicable titres may range from about 1% to about 90% in the mixture. The recovered yields of said steps are thereby at least as high as those of conventional purification methods and can approach values of 95%. The markedly good performance of a sorbent comprising residues of both kinds for the given object of the invention is even more surprising since it could be shown that sorbents comprising residues of closely related structures or only one kind of the two structures necessary showed only a moderate separation efficiency at most.

Without wishing to be bound to a theory, the high performance of this particular sorbent compared to a sorbent coated with a film of a simple, underivatised polymeric amine can be attributed to the presence of additional and structurally novel multivalent binding sites. The structures responsible for the creation of such novel binding sites can predominantly be attributed to the partial statistical modification of the polymer. Among those structures particularly to be noted is the potential presence of extended, either electron-rich or electron-poor π-systems and/or conjugated systems of weak basicity or acidity within said binding sites. The underlying interaction mode is thought to both involve interactions belonging to the group of polar/dipolar ones like electrostatic forces, charge transfer and hydrogen bonding, as well as those belonging to the group of apolar ones like hydrophobic interaction and π-stacking. The heteroatoms of the π systems are expected to be the potential sites of dipole forces and hydrogen bonding, whether through the electronic π system itself or through an extra electron lone pair. However, without having performed investigations into the actually operating mechanism in a given separation and the exact kind of the partial contribution of each residue to the overall binding strength, a definite conclusion cannot be drawn in advance for any such structure, partly because hydrogen bonding forming competition with solvent molecules may also complicate the case. Steric factors may additionally contribute to the selectivity of the designed sorbent. At least, pure ionic contributions from the first or second residues are unlikely.

Moreover, after testing a large number of differently derivatised sorbents, it was strikingly found that the presence of a third residue in addition to derivatisation of first and second portions of functional groups on the surface of the solid support material with first and second residues yielded even superior results in view of the given separation object of the invention. The solid support material may thus be further derivatised with a supplemental third, fourth, and fifth residue, and so forth. A sorbent comprising a solid support material, the surface of which in addition to first and second residues, as described above, also comprises a third residue, is therefore a further embodiment of the present invention. Pyridyl rings and carboxyl groups are being excluded as structural building blocks of the third and each further residues. Apart from this exclusion, all options regarding possible structural relationships between two residues, as exemplarily set forth in FIG. 1 for the first and second residue, analogously apply to the mutual relationships between the third and the first, the third and the second, as well as between any additional residues. Each additional residue of a different kind promotes the sorbent's potential of creating very specific binding sites for a given protein or peptide and to distinguish it from closely related side products. Each category of residues should, however, be present at a degree of derivatisation of at least about 20% since significantly lower degrees of derivatisation are in most cases negligible for statistical reasons. For the majority of applications, it is therefore sufficient to keep the number of residue categories ≤5 at about equal degrees of derivatisation. Regardless of the number and mutual ratio of different residues, each type of residue should still be homogeneously and randomly (statistically) distributed on the surface of the solid support material.

Whereas said first portion of functional groups may thereby comprise said second portion of functional groups, or may be different therefrom, the third residue may also arise from incomplete derivatisation of the surface functional groups of the solid support material with portions of first and second residues. Depending on the reagents and synthetic conditions used, the derivatisation reactions often remain incomplete. Therefore, a certain number of underivatised functional groups generic to the surface of the solid support material including the optional base polymer covering it (i.e., those incorporated into at least one of its corresponding monomers or repeating units) to be derivatised may survive intentionally or for technical reasons. These may still be accessible to various analytes, can act as supplementary part of a binding site, assist in binding the target protein or peptide, and thus add to the separation ability of the sorbent. This means that a third (leftover) portion of said functional groups itself may represent a kind of said third residues. In the present invention, it is preferred to employ solid support materials covered with a polyamine film, particularly a polyvinylamine film. Accordingly, the preferred functional groups are primary and optionally secondary amino structures which may therefore be regarded as supplemental third residues. It could also be shown in specific instances that fractions of derivatised functional groups which approach 100% led to a decrease in the selectivity for the given separation object. This fact may be taken as an indication that novel multifunctional binding sites are thus created within the sorbent comprising both first and second residues and underivatised functional groups in close spatial proximity.

By way of such a designed tertiary derivatisation or an incomplete primary and secondary derivatisation, the selectivity for a given protein or peptide can in many cases be further increased, and as an accompanying practical benefit an optional polymer film covering the surface of the solid support material is often observed to gain additional chemical stability and better solvent compatibility or swelling properties, depending on the relative polarities of the first and second residues and the functional groups involved. Nevertheless, it can be stated that the first and second residues are the most essential residues for achieving the underlying separation object in terms of specificity since a film of a completely underivatised polymer like crosslinked polyvinylamine, which exhibits only backbone primary amino functional groups to the analytes, does not achieve the separation object of the present invention satisfactorily. Ideally, the total density of residues (including underivatised functional groups acting as supplementary residues) amounts to from 0.1 mol dm$^{-3}$ to 1.0 mol dm$^{-3}$, but preferably to at least about 0.3 mol dm$^{-3}$.

On the other hand, underivatised reactive functional groups of the solid support material or of an optional polymer film thereon, more specifically amino groups, may still exhibit considerable reversible or irreversible reactivity towards the target or possible reactive side products of the mixture to be separated which may lead to firm capture of those substances—even if they are present in low concentrations only—and, after repeated use, to a slow deterioration of the sorbent and loss of binding capacity. In order to avoid such unwanted interactions, it is common practice in the preparation of chromatographic stationary phases to render such residual functional groups inactive via final <<end-capping>> of said groups. Thus, additional (third or fourth) residues may be created here via at least partial conversion of originally free functional groups into structurally different end-capped functional groups. End-capping may in this way be regarded as a special case of a derivatisation reaction establishing an improved compatibility of the solid/liquid-interface with the demands of the respective analyte, matrix, and mobile phase but which can hardly create additional binding strength and thus no additional selectivity. Partial or full end-capping of residual functional groups may nevertheless eventually turn out to be favourable in terms of long-term process stability despite the additional effort in stationary phase preparation.

Preferably, end-capping of nucleophilic functional groups such as amino groups is achieved through reactions which reduce functional group nucleophilicity. End-capping groups are designed to be of simple molecular structure so as to exhibit no interaction or at least only non-covalent and non-specific interactions of low strength with a broad range of analytes and to not alter the overall polarity of the stationary phase significantly. It is conceivable, however, that they may assist at high degrees of derivatisation the first and second residues in multivalent interactions with the substrate. Despite the possibility of more than two-fold mixed tertiary derivatisations on the sorbent due to incomplete or mixed endcapping, it has turned out that it is preferable to aim at either a uniform endcapping (i.e. to a degree >95%), or no end-capping at all, throughout the sorbent. Depending on the structure of the end-capping groups, they thus may or may not potentially act in the role of tertiary residues, if treated formally.

In a first methodical embodiment, the present invention is directed to methods for preparing sorbents of the invention having the characteristics as presented above. They will result in that special class of sorbents wherein the solid support material consists of a carrier the surface of which is covered with a film of a polymer having functional groups which are at least partially substituted with the residues. The special characteristics of this preferred class of sorbents have also been extensively outlined above. Now, said preparation methods comprise at least the steps of:

(i) providing a polymer having functional groups;
(a) adsorbing a film of the polymer onto the surface of a carrier ("adsorption step");
(b-I) crosslinking a defined portion of the functional groups of the adsorbed polymer with at least one crosslinking reagent ("crosslinkage step");
or:
(b-II) grafting a defined portion of the functional groups of the adsorbed polymer to the carrier ("grafting step");
(c) derivatising defined portions of the functional groups of the polymer with first residues comprising a pyridyl ring, whose hydrogen atoms may be substituted, and with second residues comprising a carboxyl group, and with optional further residues.

Several variations concerning the detailed layout of the above preparation method are conceivable. First, steps (b-I) and (b-II), crosslinkage and grafting, respectively, are considered as equivalent alternatives, and either one of these steps is sufficient to carry out the method in order to build up a sorbent according to the invention which will show the characteristics described further above. Both alternatives serve as means to fulfil the task of a durable fixation of the adsorbed polymer onto the carrier under the conditions of further processing and use of the sorbent, even if treated with strongly solubilising solvents. This is achieved by either forming a continuous network of additional covalent bonds between all polymer strands and thus physically entangling the carrier (crosslinkage) or by forming covalent bonds between each single polymer strand and the carrier (grafting). Of course, both alternative processes for fixation can also be combined within the method, either concurrently into a single step or subsequently as two distinguishable subordinate steps, without suffering from disadvantages for the stability of the sorbent.

Secondly, further variations are possible concerning the relative temporal order of the derivatisation step (c) in relation to the adsorption step (a). It is thus conceivable to first derivatise a polymer in homogeneous solution with the residues and then adsorb a film of the derivatised polymer already containing the residues onto a suitable carrier. Such a procedure will require to investigate and optimise the experimental conditions of the coating step for each differently derivatised polymer. The preferred variant is therefore rather to first adsorb an underivatised polymer onto the carrier as will be carried out within the adsorption step (a) parallel or prior to the derivatisation step (c), in order to obtain a thin homogeneous layer.

The crosslinkage step (b-I) or the grafting step (b-II), respectively, will in any case immediately follow the adsorption step (a) since, once crosslinked, the polymer would be difficult to be adsorbed as a film. A further boundary condition is that step (i) will always be the first step of the sequence. Taken together, the following four combinations of said two independent variations of steps (choice of step b-I or b-II combined with relative order of steps (a) and (c)) are possible:

$1^{st}$ Method: Method for preparing a sorbent according to the invention, comprising, in the following order:
(i) providing a polymer having functional groups;
(ii) adsorption step (a);
(iii) crosslinkage step (b-I);
(iv) derivatisation step (c).

$2^{nd}$ Method: Method for preparing a sorbent according to the invention, comprising, in the following order:
(i) providing a polymer having functional groups;
(ii) derivatisation step (c);
(iii) adsorption step (a);
(iv) crosslinkage step (b-I).

$3^{rd}$ Method: Method for preparing a sorbent according to the invention, comprising, in the following order:
(i) providing a polymer having functional groups;
(ii) adsorption step (a);
(iii) grafting step (b-II);
(iv) derivatisation step (c).

$4^{th}$ Method: Method for preparing a sorbent according to the invention, comprising, in the following order:
(i) providing a polymer having functional groups;
(ii) derivatisation step (c);
(iii) adsorption step (a);
(iv) grafting step (b-II).

Each step of the sequences is meant to be carried out with the polymer in its state as resulting from completion of the immediately preceding step, i.e. a derivatisation step following a crosslinkage or grafting step will be carried out with the already crosslinked or grafted polymer, whereas a derivatisation step preceding an adsorption step will be carried out with the free, non-adsorbed polymer. If a defined portion of the functional groups of the polymer is reacted in a particular step and a similar portion has already been reacted in a preceding step, it is meant that the defined portion in that particular step will be taken from the totality of those functional groups that are leftover from the preceding steps and have not been reacted previously (with the exemption of bi- or multivalent functional groups). While all four methods will in principle yield comparable results, the first method is preferred for its practical simplicity.

In a further variation which has not explicitly been mentioned so far, a first portion of the functional groups of the polymer could be derivatised in solution, the partially derivatised polymer then adsorbed, and a second portion of the same or different functional groups as before on the thus adsorbed polymer derivatised with the same or different residues as before. Or functional groups of the polymer could first be converted into different functional groups or residue precursors by solution derivatisation, which would then, after adsorption, be converted into the final residues. The most reasonable order in which individual residues are introduced by such a mixed combination of preparation steps will thereby strongly depend on the particular kind of carrier material and the easiness of adsorption of a particular, partially derivatised polymer on the carrier.

Intra- and intermolecular crosslinking of the layer will form a stable two- or preferably three-dimensional polymer network and prevent its desorption from the <<enwrapped>> carrier medium. Although crosslinking can be achieved according to all procedures known as state of the art, also incorporating unselective methods based on the generation of radical species anywhere on the polymer chains such as electrochemical, light- or (ionising) radiation-induced methods, the crosslinking step will preferably be carried out only between the functional groups of the polymer using crosslinking reagents which for example are to designed to undergo condensation reactions with said functional groups. Linear, conformationally flexible molecules, such as $\alpha,\omega$-bifunctional condensation reagents, of a length of between 1 and 20 atoms are preferred for crosslinking. Also, two or more crosslinking reagents of different length and/or different reactivity and/or different chain rigidity can be employed, preferably in consecutive steps. Crosslinking will not be carried out in an exhaustive manner which would lead to a rigid material, but always to a predetermined extent only, i.e. with a defined portion of polymer functional groups, which is easily controllable via the stoichiometric fraction of added crosslinking reagent(s) in relation to available polymer functional groups. Suitable crosslinking reagents in this respect comprise dicarboxylic acids, diamines, diols, and bis-epoxides, for example 1,10-decanedicarboxylic acid or ethyleneglycol diglycidylether (EGDGE). 4,4'-Biphenyldicarboxylic acid is useful as a rigid crosslinker.

Crosslinking reagents are preferentially chosen to react specifically with the functional groups of the polymer but neither with the template nor with the underlying carrier material such as to accomplish stable crosslinks within the polymer film only but not between the polymer film and the carrier surface. Anyway, establishing additional crosslinks of the latter type in a moderate number would certainly not alter the properties of the sorbent significantly.

If additional capping groups are desired, they are usually introduced last in the process (after the last derivatisation with a specific residue) if prior derivatisation has been incomplete. End-capping can in principle be carried out analogously to the specific derivatisation steps described above. However, activation methods leading to highly reactive reagents are usual in capping reactions since they are required to react with those functional groups which have proven to be the least reactive ones during the prior derivatisation steps. Preferred are acyl anhydrides and acyl chlorides, particularly those of acetic acid, or isocyanates and isothiocyanates, or epoxides. Also, two or more different end-capping reagents or reagents comprising two or more different capping groups such as, for example, mixed anhydrides can be employed. It can also be imagined to use other typical alkylation reagents having good leaving groups such as methyl iodide, dimethyl sulphate, or diazomethane. Other suitable end-capping methods both for polymeric and non-polymeric stationary phases as known from the prior art can analogously be used. Usually, an exhaustive end-capping of as many residual functional groups as possible is desired although the process can also be managed to stop at essentially any arbitrary degree of capping, if required.

It is also possible to temporarily derivatise functional groups of the polymer film or substituents of the residue with protecting groups. Said functional groups or substituents can thus be protected during the introduction of one or more further sets of residues from sometimes undesired reactions with the respective derivatisation reagents which may otherwise lead to uncontrollable accumulation of residues or higher-order substitution patterns such as branching. Once the additional set of residues has been put in place, the protecting groups are usually removed again.

The preferred functional groups of the polymer to be adsorbed as a film onto the surface of a carrier are primary or secondary amino groups, hydroxyl groups, and carboxylic acid or carboxylic ester groups. These groups are easily derivatisable, biocompatible, and increase the water solubility of the polymer. It is thus also preferred to employ polymers in the method which are soluble in aqueous or mixed aqueous-organic media because the adsorption step is preferably carried out from such media onto the carrier material suspended therein. Although the adsorption step itself can in principle be carried out stepwise using different polymers in each step, it is preferentially carried out with a single type of polymer (i.e., polymers having the same type of functional groups, or functional groups bearing charges of the same prefix) only. Particularly preferred are polymers having a molecular weight of between 5,000 Dalton and 50,000 Dalton.

In general, all further preferred embodiments as outlined above with respect to the composition and properties of the sorbent of the invention also apply to the methods of its preparation and the materials to be employed in said method in an analogous way and thus do not need to be repeated within this context.

The anchor group, i.e. the site of activation of the derivatisation reagent used in the derivatisation step may be close to the binding site to be formed or at a short or long distance remote from it, basically depending on structural, functional, or synthetic requirements, i.e. it may incorporate a spacer group between the structures forming the binding site and the activation site. Such spacer can be either rigid or flexible and of variable length, whereupon a longer spacer group often transforms into increased conformational flexibility which may sometimes be required by the complex between the binding site of the sorbent and the target protein or peptide in order to adopt a favourable geometry. Spacers can either be coupled first with the corresponding pyridyl ring structures and carboxyl group structures, respectively, forming the binding site in separate (possibly homogeneous) reactions and the formed conjugates, which resemble the full residues, then, after optional deprotection, coupled with the polymer, or spacers can be coupled to the polymer first and the formed conjugates then, after optional deprotection, coupled with the corresponding pyridyl ring structures and carboxyl group structures, respectively, to form the full residues. The two coupling reactions may thereby be of the same or different kind. In general, if a polymer containing primary amino functional groups is used as the film-forming polymer, the nitrogen atom of the functional amino group can directly be incorporated into the residue.

Preferred derivatisation reagents comprise amines, epoxides, carboxylic acids or esters, and iso(thio)cyanates, resulting in the formation of amide, urethane, or (thio)urea linkages with the preferred polymer functional groups. For structural, stability, and convenience reasons, it is most preferred if the derivatisation step is carried out by formation of amide bonds between the functional groups and the residues, i.e. either between an amino-containing polymer and a carboxyl-terminated derivatisation reagent or between a carboxyl-containing polymer and an amino-terminated derivatisation reagent. In conjunction with amino polymers, particularly preferred derivatisation reagents are activated carboxylic acid derivatives.

If chemical activation is necessary prior to derivatisation, it can be carried out in an extra step upstream of the derivatisation step or concurrently with the derivatisation step. Either the polymer functional groups or, preferably, the derivatisation reagent can be activated. Activation of a carboxyl group, for example, can be achieved by standard techniques of solid phase peptide synthesis, e.g. via activated esters such as OBt (benzotriazolyloxy) or ONB (norbornendicarboximidyloxy) esters. Hydroxyl groups can be treated analogously. In an economic and thus particularly preferred embodiment, the activation will be performed in situ during the derivatisation step with the help of methods also known from peptide chemistry, i.e. as a one-pot reaction in which a steady-state concentration of the activated species is being produced, but not isolated.

Both residues can be introduced into the polymer in a single derivatisation step. Optionally, a single derivatisation reagent is used here which already comprises both residues (or precursors thereof, respectively) or which comprises the first residue which comprises the second residue (or vice versa). Or at least two different derivatisation reagents are employed as a mixture, each of which comprising at least one but different residue. The derivatisation step can alternatively be carried out stepwise with each residue. Then the derivatisation reagent employed in the first derivatisation step comprises the first residue and the derivatisation reagent employed in the second derivatisation step comprises the second residue, or vice versa.

In one variation of the preparation method, derivatisation step (c) can be carried out stepwise with each kind of residue or as a single step. This embodiment takes into account that in a derivatisation reaction of the functional groups of the polymer both the first and the second residue can easily be introduced simultaneously. This can either be achieved in a way that a mixture of at least two derivatisation reagents is used, the first of which comprising the first residue, and the second one comprising the second residue. Although a random, irregular distribution of the two residues along the polymer backbone will then result, the derivatised polymer can be characterised by a statistical ratio of first and second residues which will basically be determined by the relative amounts and reactivities of the at least two derivatisation reagents. Alternatively, it is feasible to use only one derivatisation reagent if this derivatisation reagent already comprises both the first and the second residue (or if the first residue comprises the second residue, or vice versa). Naturally, both residues will then be present in the resulting derivatised polymer in a 1:1 ratio and in a pre-defined mutual regio- and stereochemistry. Instead of two fully developed residues it is also possible that at least one residue is present in the derivatisation reagent as a precursor.

Within the scope of the same variation of the preparation method of the present invention, configurations can be realised in which a mixture of derivatisation reagents is used, each of which comprising both the first and the second residue. In particular, in such a mixture a partial structure of the first residue (or precursor thereof) can be varied among the derivatisation reagents whereas the second residue (or precursor thereof) may be kept identical, or vice versa. Very particularly, derivatisation reagents can be combined with each other in pursuit of the preparation method, a defined amount of which contains both first and second residues whereas another defined amount may contain only first or only second residues. The resulting product would then exhibit one residue in excess over the other if reagent amounts and reactivities are otherwise comparable. In such way, inter alia, tailor-made, but still homogeneous and random (statistical) distributions of first and second residues among the functional groups of the polymer can be achieved.

If additional third, fourth, . . . etc. residues are to be introduced into the polymer, the derivatisation step can optionally be repeated step-wise multiple times employing further residues comprising a desired structural motif accordingly. Economically feasible are up to about four repetition steps. Preferably, each derivatisation step is always carried out to roughly the same degree of derivatisation, the degree for each residue thereby accounting for about 25%.

The sorbent of the present invention can predominantly be applied to the purification of mixtures containing proteins or peptides. In a second methodical embodiment, the present invention is therefore directed to a method of separating, or increasing the concentration and/or purity of one or more proteins or peptides from a mixture containing said protein or peptide(s) and optional side products using a target-specifically designed sorbent as described above. The method comprises at least the steps of:

(i) contacting said mixture being dissolved or suspended in a first liquid with a sorbent of the invention for a period of time sufficient to enable said protein or peptide to become bound to said sorbent;

(iii) contacting said sorbent with said bound protein or peptide with a third liquid for a period of time sufficient to enable said protein or peptide to become released from said sorbent.

In a first variation of the above method, a separate rinsing step with a second (wash) liquid that ideally does not significantly disrupt the non-covalent bonds between the sorbent residues and the protein or peptide to be purified or otherwise acts to release said sorbent-bound protein or peptide can be included between step (i) and step (iii). Depending on the kind and number of side products and further constituents contained in the mixture, such a change of liquids during the separation process can sometimes increase separation efficiency. The second liquid will mostly have low elution strength and will elute unspecifically. The method then comprises the optional intermediate step of:

(ii) rinsing said sorbent with a second liquid;

After contacting the mixture of the target protein or peptide and side products with the sorbent in step (i), the sorbent with the protein or peptide adsorbed to it can also be separated again from the remaining mixture contained in the first liquid before it is then rinsed with the second liquid in step (ii). The remaining mixture may itself be recollected if it contains valuable side products. The latter variation can also be used as a capturing means for very dilute feedstocks and also be a feasible way to remove potential side products in a rapid batch process which are suspected to interfere with a subsequent, full and more sophisticated chromatographic separation. Among such possible side products are those which may lead to a slow deterioration of the sorbent by irreversible physical or chemical adsorption and thus to shortened column durability.

In a special but important case in practice, the second liquid can be chosen identical to the first (feed, adsorption) liquid. This means that the sorbent is rinsed in step (ii) with the same liquid as the one from which the target protein or peptide is adsorbed when it is applied as a mixture to the sorbent in step (i). This is often possible since the first liquid is usually chosen such that it has only medium-to-poor solubilising properties for the target protein or peptide because an efficient adsorption will only be possible if the interaction enthalpy between the target protein or peptide and the liquid is smaller than between the target protein or peptide and the sorbent. If, on the other hand, this liquid has good solubilising properties for the side products which are supposed to be eluted from the sorbent in step (ii), it can also be applied for rinsing the sorbent while the target protein or peptide will still adhere to it without being simultaneously released.

Similarly, the second liquid can be chosen identical to the third (desorption, elution) liquid. If the solubilising properties of the third liquid for the target protein or peptide and the side products are different to a degree large enough while their adsorption enthalpies on the sorbent are comparable, the same liquid can be used for rinsing the sorbent. This essentially means that step (ii) and step (iii) of the method can under these circumstances be combined into one step. In a continuous flow system, the better solubilised side products will then be rinsed off first, followed by the released target protein or peptide in a later eluted fraction of the same liquid. Of course, this sequence may again be followed by additional fractions of the third liquid containing further, less solubilised and therefore slower eluted side products.

Even all three liquids may be identical. However, even if two or three liquids are chosen identical, they may still be applied to the sorbent at different flow rates in different steps of the method. Volumetric flow rates in chromatography are in general a function of the applied pressure regime, the column dimensions, and the liquid viscosity. Corresponding one-dimensional velocities of the mobile phase in HPLC are typically in the order of about 1-5 mm s$^{-1}$. The numeration first, second, third, . . . liquid thus serves to define the relative sequence of applying liquids that fulfil different tasks, but is not meant to define necessarily particular compositions of the respective liquids. Instead of exchanging the kind of liquid or its applied flow-rate discretely or stepwise (i.e., as a step-gradient), other continuous gradient shapes, in particular linear gradients, may be used to switch slowly between the different liquids and/or flow rates. This requires an at least partial mutual miscibility of the liquids and the installation of a mechanism to gradually mix increasing fractions of the succeeding liquid into the preceding liquid, respectively.

In one embodiment of the present invention, the third liquid will differ from the first and optionally also from the second liquid in its pH. In a particular embodiment, the pH of the third liquid is higher than the pH of the first and optionally of the second liquid. Still more preferred, the pH of the third liquid is close to (i.e.: within ±1 unit approximately matches) the isoelectric point pI of the target protein or peptide, whereas the first and optionally the second liquid has a pH which is largely different therefrom, at least by ca. 2 pH units, and in particular lower. The pH of the first liquid may favourably be in the range of from 4.0 to 6.0 whereas the resulting pH of the third liquid would be in the range of from 6.5 to 8.5. This embodiment deals with the case that the enthalpy of binding between the sorbent and the target protein or peptide is dominated to a significant part by electrostatic or other polar interactions (dipole forces, hydrogen bonds) involving one or more ionisable residues (e.g. amino groups, nitrogen-containing pyridyl rings or oxygen-containing carboxylic groups) on either binding partner. In particular, hydrophobic and polar interactions are expected to be dominant close to neutral pH, whereas ionic repulsion is expected to partially replace the attracting polar forces of the same, hitherto uncharged residues, when approaching either extreme of the pH spectrum (e.g., between protonated nitrogens at low pH or deprotonated oxygens at high pH). This effect can considerably weaken the enthalpy of binding and, as a result, release the bound protein or peptide from the sorbent or hinder side products from binding to it. In the opposite way, an attractive ionic interaction can also be weakened upon loss of a point charge of either binding partner as a result of a pH shift. Of particular importance are in this respect nitrogen-containing heteroaromatics such as pyridines as residues on the sorbent since these are capable of exhibiting both hydrophobic as well as polar/ionic interactions. The attractiveness of such pyridyl rings for use in the separation method of the invention results from the fact that their binding behaviour can be switched at pH values which closely resemble physiological conditions, whereby the exact pH range of switching is dependent on the isoelectric point of the specific residue and may thus be fine-tuned by its structure and the relative composition of the sorbent which contains at least two different ionogenic residues. On the other hand, the pH dependency of the enthalpy of binding may as well apply with regard to interactions between the sorbent and at least one side product to be separated off. This can for example be due to different isoelectric points of target and side products or to quantitatively different relative contributions of hydrophobic/polar vs. electrostatic interactions.

In a further embodiment of the present invention, the third liquid will differ from the first and optionally also from the second liquid in its ionic strength. In a particular embodiment, the ionic strength of the third liquid is higher than the ionic strength of the first and optionally the second liquid. This embodiment deals with the case that the enthalpy of binding between the sorbent and the target protein or peptide is dominated to a significant part by electrostatic interactions under participation of one or more ionic or ionisable residues, whereas such participation is different, in particular less pronounced, in the electrostatic interaction between the sorbent and at least one side product to be separated off. On the other hand, hydrophobic contributions to the enthalpy of binding will be strengthened upon an increase in ionic strength, if all other parameters are kept constant. Preferably, the adsorption step (i) of the separation method is performed under low-salt conditions (0-0.2 M sodium chloride) in the first liquid, whereas the release step (iii) can be performed at up to 1 M sodium chloride in the third liquid. Although the sorbent of the invention tolerates high-salt conditions very well, it is under most circumstances neither necessary nor advisable to add high salt concentrations to the third liquid of step (iii) in order to desorb sorbent-bound proteins or peptides. Instead, the affinity of the sorbent for many proteins or peptides can be largely invariable with changes in salt concentration. Therefore salt gradients may not be effective merely by themselves to release adsorbed proteins or peptides, but they can be efficient in combination with assistive pH gradients.

Release of the target protein or peptide from the sorbent can thus be accomplished via increasing the solvation strength of the third liquid for the target as compared to the first and second liquids. It can alternatively be accomplished via displacement of the target protein or peptide from the binding sites of the sorbent with a displacement reagent which is dissolved in the third liquid. The displacement effect (preferable binding of the displacement reagent by the sorbent rather than of the competing target) can either be achieved if the displacement reagent is present in molar excess over the target protein or peptide or if the displacement reagent's binding strength toward the sorbent is even higher than that of the target protein or peptide. The displacement reagent may itself be a protein or peptide having similar properties as the target, or a fragment thereof, but also a small synthetic molecule with high affinity for pyridyl residues and carboxyl residues.

Another eluent change, after the target protein or peptide has become completely released from the sorbent, can similarly be useful in terms of economics in order to accelerate a chromatographic run at the expense of chromatographic resolution, or if other valuable products are eluted behind.

In a second variation, the method is augmented by the optional final step of:
(iv) washing and/or regenerating the sorbent with a fourth and/or fifth liquid;
which is introduced after step (iii).

Here, as a fourth (cleaning) liquid a liquid is used which will mostly have very high elution strength, may contain additives of the above-mentioned kind, and elute unspecifically. If the sorbent is used in the form of a chromatographic column, the fourth liquid may be applied at high volumetric flow rates in the normal or reverse direction since its task is to clean the sorbent and permanently remove any build-up of residual, strongly adsorbing or otherwise interfering chemical or biological impurities, especially particulate matter, in order to prevent gradual fouling, clogging, or capacity reduction of the column. For medical hygiene and safety, typical sanitisation or sterilisation protocols (e.g., alkaline (1.0 M sodium hydroxide), acidic (0.4 M acetic acid), oxidative (hypochlorite) and/or heat treatment) to eliminate microbial contamination can also be applied to the sorbent at this point.

The fifth (reconditioning) liquid is used to condition the sorbent, its degree of swelling, and the solvation of its attached residues after prior treatment with aggressive or strongly solvating liquids such that the original state of the sorbent is restored and constant, equilibrated conditions are installed at the beginning of each separation run. Apart from the removal of traces of elution or cleaning liquids, counterions of ionic residues, if present, will thereby also be replaced to their original uniform distribution in order to maintain constant acid/base properties of the sorbent. The fifth liquid can be identical to the first or second liquid, and will usually be applied at the same flow rate. It is also possible to switch from a quick and simple wash/regeneration program after each run to a more sophisticated procedure after every fifth, tenth etc. run, for example, depending on the actual load of those contaminants which are critical to reach the attempted product quality specifications.

The preferred way of carrying out the separation method is as a medium-to-high pressure liquid chromatography technique. Due to its operational simplicity, and by way of either of the variety of variations cited above, the method may also be used discontinuously in the manner of a batch purification as with the affinity (membrane-) filtration or solid phase extraction techniques or continuously as with the simulated moving-bed (SMB) technique. All variations may also be combined with one another.

The strong chemical stability as well as static and dynamic binding capacity of the sorbent (up to ca. 0.3 l feed load or ca. 20 g protein or peptide per liter of sorbent, respectively, are possible) allows large degrees of freedom in the independent variability of all five liquids used in the method. Also strongly solvating eluent systems not compatible with conventional affinity chromatography are now accessible so that there is plenty of room to optimise the liquids for properties such as solubilising power, low cost, low toxicity, and low waste production. A system of liquids compatible with the implementation of the method basically comprises any liquid or mixture of liquids which possesses at least weak solubilising properties for the substrate of the separation method, i.e. in particular a protein or peptide, and preferably also for the side products—the latter being of particular importance for the second liquid. Since chromatographic separations on the sorbent of the present invention will usually be carried out under biocompatibility restrictions, buffered aqueous media are often used as first, second, and third liquids. Organic modifiers other than buffers or metal salts which are essential to preserve the protein function (e.g. detergents, chaotropic additives, antioxidants, antifoams) could hypothetically also be added to the liquids, but in order to retain the highest possible biological activity of the protein or peptide to be purified, these reagents are best be avoided completely. Small amounts of volatile organic acids may be added though prior or subsequent to the actual separation process for reasons of enhancing the detectability of certain analytes.

If further additives are being used nevertheless, they usually have to be removed later on, i.e. after completion of the method, from the liquid containing the target protein or peptide obtained in step (iii), especially if it is required to obtain said protein or peptide in crystalline form. To achieve this purpose, a broad range of such potentially additional steps is well known to those skilled in the art. In order to remove additives, the method of the invention may therefore as well be combined subsequently with any other type of common separation processes.

Though it would be feasible to apply virtually any organic or aqueous liquid or liquid mixture including supercritical fluids to the sorbent of the present invention, preference is given to those polar liquids which facilitate swelling of a polymer film, if present on the surface of the solid support material. The exact polarity of a liquid mixture can be easily fine-tuned by way of its composition.

Since the adsorbed target protein or peptide (and also side products) are often not released instantaneously (like an on-off state) in step (iii) of the method but rather slowly and gradually, step (iii) itself can favourably be carried out stepwise, i.e. as a fractionation, for an increased resolution of the overall separation process. Two or more fixed-volume fractions of either the same or different size are then collected manually or automatically of the third liquid after the sorbent has been contacted with it for a sufficient time. Then step (iii) is repeated and the sorbent is again contacted with fresh third liquid (of a modified composition, if necessary) until all bound target protein or peptide has been released. A continuous supply of the third liquid is also realisable during the collection of fractions. Purity and recovery of the released target protein or peptide in each fraction is subsequently determined, and only those fractions which meet the pre-set acceptance specifications in terms of quality and/or economy are further processed while all other fractions may either be discarded or recycled into the feedstock.

Frontal as well as zonal elution techniques can be employed. The best performance and productivity are often achieved with gradient elution, especially with increasing content of polar organic solvents (lower alcohols, acetonitrile, acetone) to the second and/or third liquids. However, if used in process chromatography or within a manufacturing environment in general, isocratic elution or simple gradient shapes such as step gradients might be preferred for operational simplicity and technical robustness. pH and salt gradients can also be successfully implemented. Depending on the particular residues of the sorbent, pH values in the range between 1 and 14 for short durations, and between 2 and 13 for continuous operation, are possible, as far as the chemical stability of the sorbent is concerned. The respective optimum liquid compositions will also depend on the actual degree of derivatisation of the sorbent and has to be determined experimentally from case to case.

What makes the method clearly distinguishable from conventional ion exchange sorption is that it can also and particularly be applied to separation tasks in which the protein or peptide does not contain any net ionic charge, i.e. if the pH of the solubilising medium resembles closely its isoelectric point. Although ionic charges of any prefix may add to the binding strength toward the sorbent of the present invention due to its content of protonable nitrogen- and deprotonable oxygen-containing residues, their presence is not obligatory for a successful completion of the method. The same holds true for the side products and other components of the mixture. The extent to which charged interactions are able to affect the sorption or separation of a compound on a sorbent is also determined by the dipolar character and salt concentration of the surrounding medium. What has been explained above for opposite charges of sorbent and analytes is also true for charges of the same prefix which may lead in some cases to repellence and exclusion from the sorbent instead of an additional attraction.

The method may also additionally comprise the isolation of the protein or peptide, subsequent to step (iii), from at least one fraction of the third liquid into which it has there been released. In preparative applications, it is possible to isolate the protein or peptide in concentrated or even neat form from a solution in the third liquid for the purpose of characterisation and/or subsequent treatment. In the easiest way, it can be recovered from the liquid of step (iii) by gentle methods of solvent evaporation (including freeze drying, lyophilisation). Solvent evaporation would, however, also enrich possibly contained substances of low vapour pressure stemming from the third liquid. Such substances may comprise additives such as buffer salts or stabilising agents, or contaminants such as higher boiling solvent homologues and/or degradation products which are usually contained in trace amounts in solvents of commercially available qualities. Due to the high physical and chemical stability of the sorbent, however, practically no leaching from the stationary phase will occur during steps (ii)-(iv), so that the released protein or peptide of step (iii) will typically contain less than 10 ppm of leached sorbent or other leachable substances therefrom (i.e. its constituents (polymer, residues), or decomposition products).

A preferable method of isolation consists of a crystallisation step of the third liquid containing the purified protein or peptide or said evaporated residue, if necessary, after re-dissolution. During such a crystallisation step, which may for example be induced by changing the temperature and/or the composition of the liquid, even higher degrees of purification can be achieved since contaminants of low vapour pressure are usually kept in solution and are thus easily separated from the targeted product crystals. After drying, the crystals are often ready for use in compounding and formulation processes. If dry storage is unwanted or impossible, it may alternatively be necessary to perform a transfer of the purified product into a solution of differing composition, i.e. the third liquid would be exchanged against a storage liquid by standard operations like dialysis, ion exchange etc.

As usual in chromatography, the method and an associated apparatus on which it is run may also favourably be supplemented by a suitable detection technique which allows for qualitative, semi-quantitative or quantitative measurement of the concentration of the target protein or peptide and/or side products or other components of the mixture in the eluate for sharp and fine fractionation. Preferred detection methods involve on-line flow-cell detectors of physical or spectroscopic properties such as refractometers, polarimeters, conductometers, ultraviolet/visible absorbance or fluorescence spectrometers, infrared spectrometers, mass spectrometers, and nuclear magnetic resonance spectrometers. An online pre- or post-column derivatisation or degradation unit may also be added to the system in order to convert all or specific components of the mixture to be separated into derivatives or fragments with improved detectability, or to accelerate or delay their elution. A universal non-destructive detection method for proteins or peptides is UV absorbance at a wavelength of 280 nm.

On the large scale, the sorbent and thus also the separation method of the present invention employing the sorbent can beneficially be used in the manufacture of a pharmaceutical or nutritional composition for human or veterinary use (e.g. an antiserum or vaccine), if such composition comprises at least one protein or peptide of diagnostic, therapeutic, or nutritional value which can be bound by the sorbent. The benefit of the present invention mainly arises from the fact that such applications often require purities of the valuable active ingredient in the range of >99% or even >99.9% which are realisable by conventional methods only under lengthy and costly procedures, which may even render some applications prohibitive from an economic viewpoint.

On the small scale, they can alternatively be used in the identification, characterisation, quantification, or laboratory purification of the at least one protein or peptide. For this purpose, which is related to qualitative and quantitative analysis, the separation method is likely to be complemented by a specific biological assay or by a spectroscopic method, e.g. using hyphenated techniques, but can also be accomplished by comparison of retention volumes with pure, authentic samples or peptide standards. In microscale formats, they may be interesting for proteomic applications, i.e. the simultaneous identification or quantification of the expression levels and modifications of a plurality of different proteins in a cell or in an organism.

As part of a medical device, they can also be used in the removal of at least one protein or peptide from a biological fluid, which includes the medical prevention or treatment of diseases being caused by the presence of said at least one protein or peptide in said biological fluid. The device may be applied as a kind of detoxification or decontamination unit in all cases in which a patient has already taken up or is about to take up harmful or infectious proteins or peptides, as they are for example secreted by pathogens, but also in those cases in which the body of the patient itself has produced such harmful or infectious proteins, as it is often the case in autoimmune diseases. Potential sources of uptake include food, water, air, contact with infected persons, blood transfusions etc. In a specialised application, the medical device may be constructed as an apheresis or plasmapheresis unit. Such a device will predominantly be operated ex-vivo or in-vitro, but construction as a miniaturised, implantable device also appears to be within imagination. A biological fluid of the patient could (either continuously or batch-wise) be taken from the patient, depleted from the contaminant via treatment with the sorbent, and then returned to the patient. Biological fluids from external sources (other humans, animals) could also be treated with the sorbent to reduce the risk of transmission of infectious diseases before the fluids or parts thereof or compositions manufactured therefrom are administered to a patient in need thereof. In such case, the separation method of the invention would be used to diminish the concentration/purity of the target protein or peptide in the <value> fraction (thereby increasing the purity of the proteins or peptides of value therein), whereas it would be enriched in the <waste> fraction.

Finally, they can be used for the immobilisation of at least one protein or peptide on the sorbent. Due to the non-covalent nature of the interactions between the sorbent and the targeted protein or peptide, such immobilisation will be reversible. This may be a potential advantage in applications such as the preparation of filterable reagents or catalysts, the surface-bound culture of cells, in drug delivery devices (e.g. drug eluting or healing stents), or in drug discovery screenings. In the latter case, the separation method of the invention can be complemented by a method of testing for binding of further chemical or biological structures to the immobilised protein or peptide. The detection of such secondary binding can then serve as a first indication of a possible physiological effect of either binding partner. If a polymer coating is used, the immobilised protein or peptide may become physically entrapped by the surrounding gel-forming medium and will thus additionally experience an environment of high biocompatibility. Expressed differently, a non-covalent, isolable complex formed between a sorbent as described herein and at least one protein or peptide is thus also embodied within the present invention. Such a complex containing an antibody as the preferred protein of the invention may be used in immunosorption techniques.

A further object of the present invention which can immediately be derived from the explanations given above is a pre-packed column, comprising a sorbent of the present invention within a tubular containment. Such a column can be used as stationary phase of a fixed, desired size (length× diameter) in liquid chromatography or solid phase extraction applications. Beside the tubular containment, such a column can optionally comprise further components such as frits, filter plates, flow distributors, seals, fittings, screwings, valves, or other fluid handling or connection elements, which are known from the state of the art. The sorbent may be packed either as a slurry under gravitational or centrifugal force, under externally applied hydrodynamic pressure, or under additional axial compression by a piston into the column, and made commercially available in such a pre-packed format. For the added convenience of the user, a more reproducible packing can thus be assured and stationary phases can easily be stored if not in use and quickly be exchanged within a chromatographic system. The material the containment is made of (chemically and biologically inert materials such as stainless steel, borosilicate glass, plastics like PEEK etc.) is typically chosen such that the high stability of the sorbent itself is not sacrificed, which means that the entire column should ideally be characterised by a physical and chemical resistance against applied pressures up to 20 bar or against applied heat up to 110° C. as well as against common sanitisation protocols including autoclavability. Under favourable circumstances, this will enable a repetitive use of the column of up to 1,000 times, preferably up to 5,000 times, and add to overall process economy. However, it can also be a disposable or incinerable unit. Another option is to design only the immediate tubular housing of the sorbent cheap and disposable and to place it inside a second, outer housing made of long-lived and durable materials which also contains all re-usable, supplementary components (cartridge design).

A column can be part of a full chromatography system. Apart from the detection system described above, other pertinent components of a chromatography system include pumps, flow regulators, liquid reservoirs, degassers, injection ports, column switching valves, pressure and flow meters, temperature-controlled chambers, outlet collection trays (carousels), and robotic fractionators.

A further object of the present invention is a collection (or "library") of a plurality of the same or different sorbents of the present invention either as loose materials (of granular or block (monolithic) design) or as pre-packed columns, cartridges (see above), or membranes, whereby the individual sorbents may be the same or different. A collection of different sorbents may for example be used in an initial screening campaign for suitable sorbents that are planned to be used in a more sophisticated preparative chromatographic setup afterwards, whereas a collection of the same sorbents may for example be used in multiple medical diagnostic tests of large numbers of samples having similar matrixes, or in quasi-continuous process monitoring. The advantage of such a collection is its ability to be processed in parallel, either in a manual or in a automated fashion. Such parallel processing allows—beside time savings due to higher sample throughput as compared to serial processing—to compare different sorbents or other process parameters also under standardised or at least identical (reproducible) conditions. This advantage can especially be exploited if the individual members of the collection are arranged in a standardised and positionally addressable format, preferably a two-dimensional rectangular grid compatible with robotic workstations, such as a microplate array or a microchip array, or as a multi-capillary or microfluidic device. As far as the readout of miniaturised formats is regarded, reference is made again to proteomics technologies.

All intermediate products beginning with the crosslinkage/ grafting step of the preparation methods described above are sufficiently stable to be stored for future usage. Such product can then be split into several subsets upon which the derivatisation step is performed with individual derivatisation reagents. In such way a library of different sorbents (i.e. sorbents derivatised with different residues or combinations thereof or at different residue ratios or different degrees of derivatisation) can be formed on demand. If the derivatisation step is carried out in parallel on the entirety of subsets, it is feasible to form such a library in a very short time in order to perform an initial screening search of the best sorbent for a given application which would allow to respond rapidly to changing separation objects. Apart from different derivatisations, different solid support materials, including the possibility of different polymer films, carriers and/or activation chemistries, may also be applied in the formation of the sorbent library.

Random or targeted library screening is a means which may sometimes complement or even replace rational sorbent design. It is used especially in those cases where the relative importance of contributions from different residues on the sorbent and/or their counterparts on the target protein or peptide are non-obvious, if structural information is scarce, or if additional tight boundaries, e.g. concerning the choice of compatible liquid phases, apply. The screening of such a library toward a given separation object can be carried out in such a way that one or more parameters that characterise the performance of a particular sorbent (affinity, selectivity, capacity, recovery, stability etc.) are measured either consecutively or in parallel with the full library or one or more subsets thereof. The most prominent characteristics are affinity- and selectivity-related thermodynamic and kinetic parameters regarding the formation of complexes between the sorbent and protein or peptide targets. A pre-selection of sorbents suitable for incorporation into the library could be performed with computational methods.

A viable screening method would for example consist of treating a mixture containing at least one protein or peptide as well as side products and/or other components with the respective sorbents of the present invention under suitable batch conditions and measure the individual equilibrium Gibbs enthalpies of complex formation between the sorbents and the targeted protein or peptide. An alternative method would consist of measuring the differential Gibbs enthalpies between the formation of complexes of the sorbent with the targeted protein or peptide on one hand and those with appropriately chosen side products on the other hand. Measurements can directly be carried out with the help of all thermodynamic and/or kinetic methods known to the person skilled in the art such as, e.g., calorimetry. Measurements can also be made indirectly with the help of chromatographic runs under the process-like conditions of the envisaged application on the transient formation of such complexes, whereby the obtained results may need to be corrected for eluent contributions. In a chromatographic environment, k' and α values may serve at first approximation as indicators of the Gibbs enthalpy or differential Gibbs enthalpy, respectively.

A further object of the present invention is a diagnostic or laboratory purification kit, which comprises beside a sorbent of the invention (or a collection of sorbents, or a column containing the sorbent), within the same packaging unit, a set of further (or even all) chemical or biological reagents and/or disposables necessary for carrying out the separation method of the invention or a different analytical, diagnostic, or laboratory method in which said sorbent can be employed. Such a pre-packed collection of materials in the right number, amount, or concentration is intended to increase the convenience of the user if standardised experimental protocols have to be followed when the separation method is carried out, and especially if the sorbent or column is used as a disposable device. Said protocol can be incorporated together with safety data sheets etc. into the directions for use which can optionally accompany the kit.

BRIEF DESCRIPTION OF THE DRAWINGS

FIG. 1: Different individual configurations A-H and one general representation I resulting from derivatisation of two adjacent surface functional groups (FG) with one first and one second residue.

FIG. 2: Different schematic morphologies A-C of a solid support material consisting of a carrier the surface of which is covered with a film of a polymer (here exemplified for a non-porous, particulate carrier depicted as a grey sphere; not drawn to scale).

EXAMPLES

Materials and Methods

Figure 3:
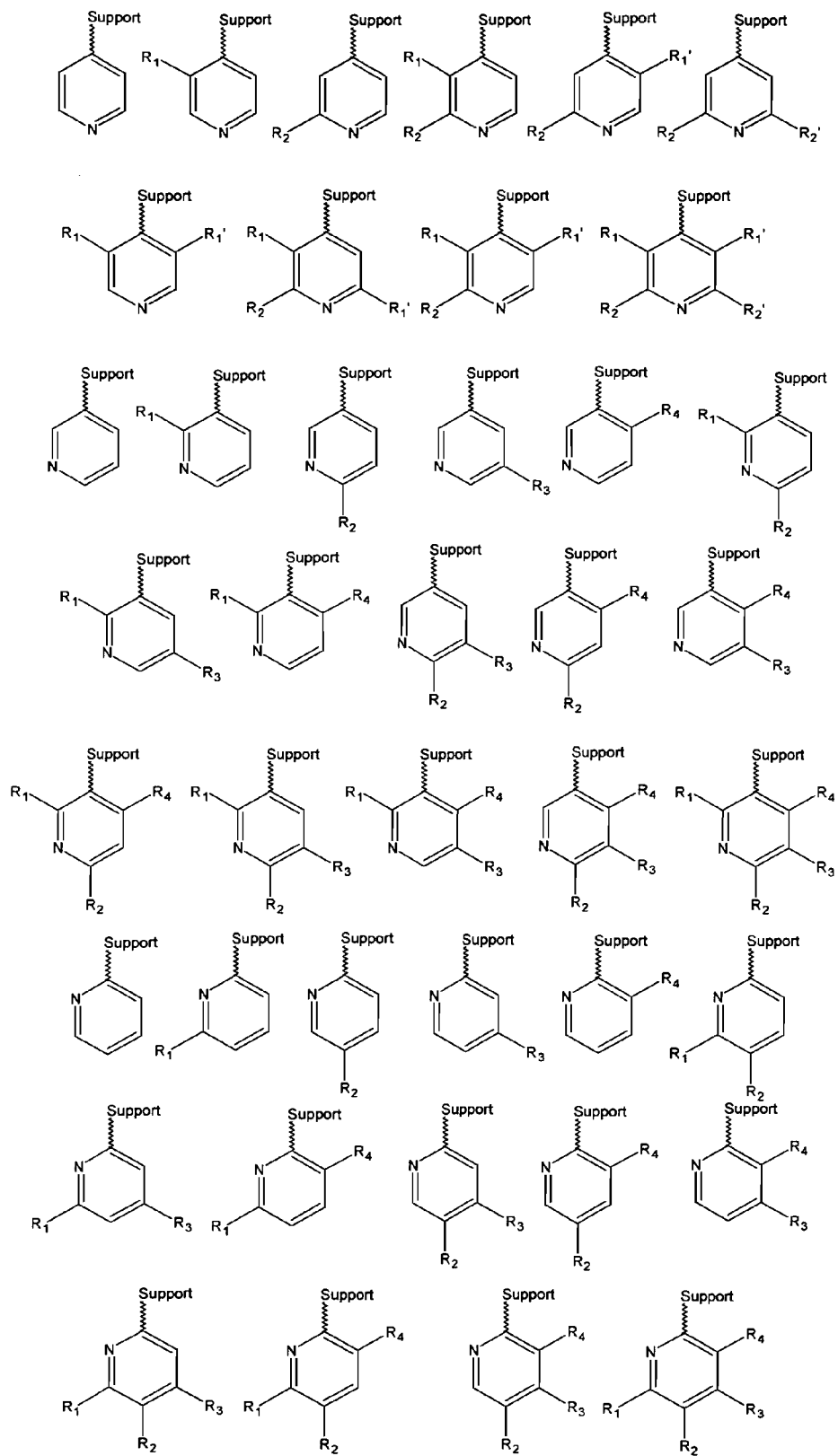
FIG. 3: Choice of possible substitution patterns of first residues comprising a pyridyl ring whose hydrogen atoms are substituted.
Figure 4:
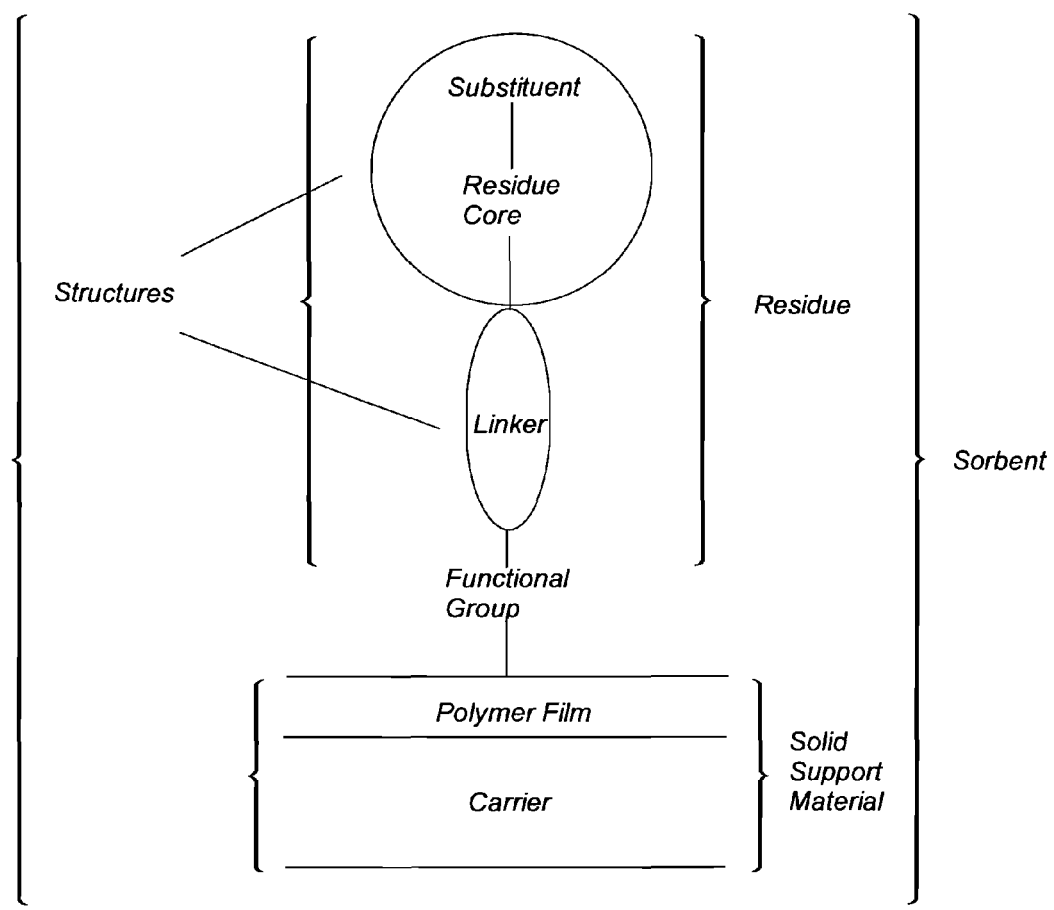
FIG. 4: Symbolic representation (not drawn to scale) of terms used to characterise the analyte-interacting surface of the sorbent. Not all items depicted are necessary to carry out the invention.
Figure 5:
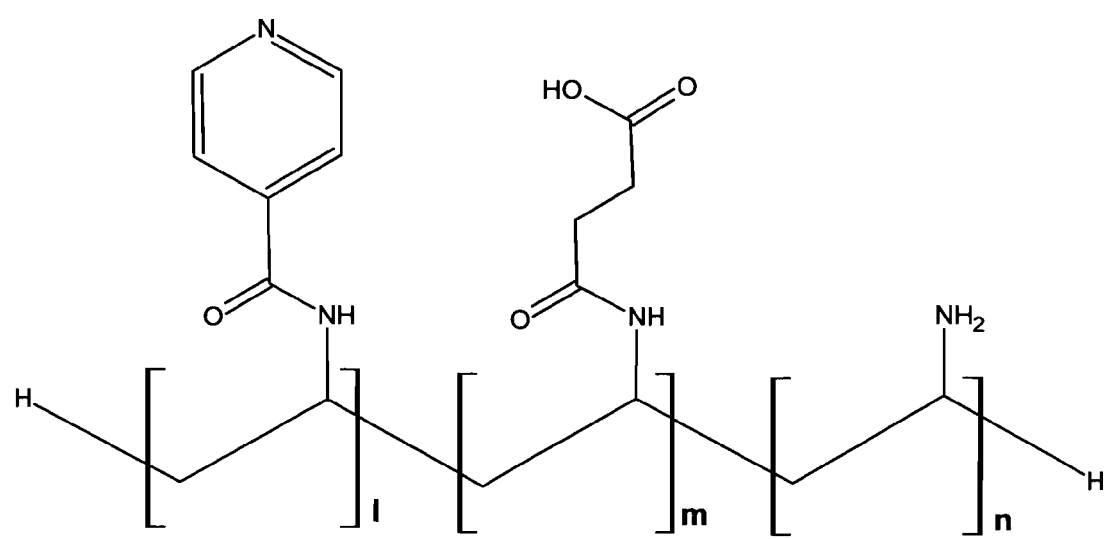
FIG. 5: Symbolic representation of a sorbent according to the invention comprising a polymer which is a polyvinyl amine which is partially derivatised with the first and the second residue as defined in said Figure, wherein l, m, and n represent figures which are independent from each other, each indicating repeating units.

The sorbents were used for all chromatographic experiments in standard stainless steel HPLC columns of 40×4 mm actual bed size (Example 2) or Götec glass columns of 250× 16 mm actual bed size (Example 3). Columns were packed by flow sedimentation of water-methanol (1:1) suspensions under a pressure of 20 bar.

HPLC systems from Dionex (formerly Gynkotek) consisted of a four channel low-pressure gradient pump (LPG 580, LPG 680 or LPG 3400), auto sampler (Gina 50, ASI-100 or WPS-300), six-channel column switching valves (Besta), column oven and a diode-array UV detector (UVD 170U, UVD 340S or VWD 3400). For preparative runs, an Äkta Purifier 10 (GE Healthcare) unit was available.

Immunoglobulin G (Octapharma (Gammanorm®), source: human plasma) had a molecular weight of 144 kDa and an isoelectric point pI of 6.4. Human serum albumin (Octapharma (Octalbin® 20% solution), source: human plasma) had a molecular weight of 66 kDa and an isoelectric point of 4.6. All other reagents used were of standard laboratory grade quality.

Example 1

Preparation of the Sorbents

Commercial polystyrene-divinylbenzene copolymer spherical resin beads (Rohm & Haas Company: Amberchrom™ CG1000S) were first excessively sulphonated in concentrated sulphuric acid, then commercial polyvinylamine-polyvinylformamide copolymer solution (BASF: Lupamin®) was adsorbed onto the porous beads and lightly chemically crosslinked with a bis-epoxide. To this underivatised intermediate, which contained approx. 0.35-0.45 mmol/ml free amino groups and was pre-swollen in dimethyl formamide, in situ-activated isonicotinic acid was coupled to the amino groups via a standard solid phase amide coupling protocol in a slight excess over the predetermined amount corresponding to the targeted degrees of derivatisation. In a second step succinic anhydride was added to the phase suspension also in a slight excess to obtain the specified grade of derivatisation of amido linked carboxylic acids. The sorbents were washed free of excessive reagents and dried until constant weight was achieved. Degrees of derivatisation were determined after each derivatisation step via hydrolytic cleavage and quantitative analysis of the cleaved residues by HPLC. The degree of derivatisation was defined as ratio of cleaved groups compared to the amount of measurable amino groups of the underivatized intermediate. According to this general procedure, the sorbents listed in Table 1 were prepared. The accuracy in derivatisation was approx. ±2%. The difference between the combined degrees of substitution and 100% equals the content of residual amino groups.

Example 2

Chromatography of a Standardized Test Mixture Containing IgG and HSA

125 μL of a mixture of commercially available human immunoglobulin (IgG) and human serum albumin (HSA) were injected in a 5:1 proportion onto the columns. This related to a loading of 7.2 mg total protein per mL sorbent material, respectively approx. 6 mg/mL IgG and 1.2 mg/mL HSA per mL sorbent. The protein proportion which was not bound to the sorbent was collected (flow) and was analyzed and quantified by means of gel permeation chromatography. By means of a standardized IgG and HSA, the presence of HSA (partial failure to bind), respectively the absence (binding) of IgG in the flow could be verified. By means of a HSA calibration function on the gel permeation chromatography column, the HSA could be verified in the flow which was not bound. IgG was completely bound in all tested sorbents. HSA was quantified in the flow with 50 to 90% of the feed quantity. In Table 1, the amount and proportion data of the two proteins found in this analysis are opposed to the structural compositions of the corresponding sorbents.

TABLE 1

Results of Examples 1 and 2

| Sorbent # | Isonicotinic acid Derivatization [%] | Succinic acid Derivatization [%] | Amount of injected HSA [mg] | Amount of injected IgG [mg] | Amount of HSA in the flow [mg] | Proportion of HSA in the flow [%] | Proportion of IgG in the flow [%] |
|---|---|---|---|---|---|---|---|
| 1 | 42 | 29 | 0.5 | 2.5 | 0.32 | 64 | Not detected (nd) |
| 2 | 42 | 28 | 0.5 | 2.5 | 0.26 | 52 | (nd) |
| 3 | 39 | 52 | 0.5 | 2.5 | 0.33 | 66 | (nd) |
| 4 | 36 | 31 | 0.5 | 2.5 | 0.33 | 66 | (nd) |
| 5 | 36 | 28 | 0.5 | 2.5 | 0.34 | 68 | (nd) |
| 6 | 39 | 56 | 0.5 | 2.5 | 0.44 | 88 | (nd) |
| 7 | 36 | 30 | 0.5 | 2.5 | 0.36 | 72 | (nd) |
| 8 | 39 | 51 | 0.5 | 2.5 | 0.38 | 76 | (nd) |
| 9 | 36 | 37 | 0.5 | 2.5 | 0.39 | 78 | (nd) |
| 10 | 36 | 30 | 0.5 | 2.5 | 0.25 | 50 | (nd) |
| 11 | 33 | 48 | 0.5 | 2.5 | 0.42 | 84 | (nd) |
| 12 | 39 | 44 | 0.5 | 2.5 | 0.42 | 84 | (nd) |
| 13 | 38 | 53 | 0.5 | 2.5 | 0.28 | 56 | (nd) |
| 14 | 39 | 55 | 0.5 | 2.5 | 0.27 | 54 | (nd) |
| 15 | 40 | 60 | 0.5 | 2.5 | 0.28 | 56 | (nd) |
| 16 | 36 | 52 | 0.5 | 2.5 | 0.28 | 56 | (nd) |
| 17 | 36 | 57 | 0.5 | 2.5 | 0.30 | 60 | (nd) |
| 18 | 40 | 59 | 0.5 | 2.5 | 0.37 | 74 | (nd) |

The invention claimed is:

1. A sorbent comprising a solid support material, wherein the solid support material surface comprises a first residue which is a pyridine-4-carboxamido (isonicotinic amide) residue having the structure of formula I, and a second residue which is a 3-carboxamidopropionic acid (succinic monoamide) residue having the structure of formula II,

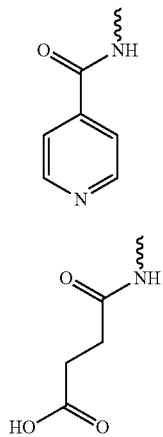

wherein the first and/or second residue are attached to the support material surface via a covalently bonded conformationally flexible linker having a length of between 1 and 20 atoms.

2. The sorbent of claim 1, wherein the solid support material surface additionally comprises a third residue and, optionally, a fourth residue.

3. The sorbent of claim 2, wherein the third residue comprises an amine or an amide structure.

4. The sorbent of claim 2, wherein the third residue comprises a primary amine structure.

5. The sorbent of claim 1, wherein the first and second residues are present at a molar percentage of between 25% and 75%, and of between 20% and 60%, respectively, based on the total molar amount of all residues present on the surface of the sorbent.

6. The sorbent of claim 1, wherein the first and second residues are present at a molar percentage of between 25% and 60%, and of between 20% and 50%, respectively, based on the total molar amount of all residues resent on the surface of the sorbent.

7. The sorbent of claim 1, wherein the first and second residues are present at a molar percentage of between 25% to 40%, and of between 20% to 30% respectively, based the tote molar amount of all residues present on the surface of the sorbent.

8. A sorbent comprising a solid support material, wherein the solid material comprises a carrier comprising a polystyrene sultanate, wherein the surface of the carrier is covered with a film of a polymer having functional groups which are at least partially substituted with a first residue comprising a pyridyl ring (—$C_5H_4N$), wherein the hydrogen atoms of the pyridyl ring may be substituted, and a second residue comprising a carboxyl group (—COOH), and optionally a third and fourth residue(s).

9. The sorbent of claim 8, wherein the carrier is a polystyrene sultanate.

10. The sorbent of claim 8, wherein the polymer consists of individual chains which are covalently crosslinked with each other, but which are not covalently grafted to the surface of the carrier.

11. A sorbent comprising a solid support material, wherein the solid support material comprises a carrier, wherein the surface of the carrier is covered with a film of a polymer having functional groups which are at least partially substituted with a first residue comprising a pyridyl ring (—$C_5H_4N$), wherein the hydrogen atoms of the pyridyl ring may be substituted, and a second residue comprising a carboxyl group (—COOH) and optionally a third and fourth residue(s), wherein the polymer is a partially derivatized polyamine selected from polyvinylamine, any partially derivatized copolymer comprising a polyamine and any partially derivatized copolymer comprising a polymer blend comprising a polyamine.

12. The sorbent of claim 11, wherein the polymer is polyvinylamine which is substituted by a first residue having the structure of formula I, and a second residue having the structure of formula II,

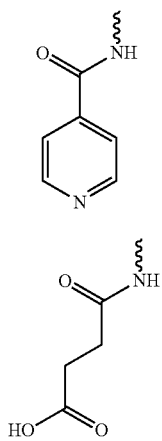

wherein the NH group within the structures of formula I and formula II derives from the polyvinylamine.

13. A method for preparing the sorbent of claim 8, comprising:
   (i) providing a polymer having functional groups;
   (ii) adsorbing a film of the polymer onto the surface of a carrier;
   (iii) crosslinking a defined portion of the functional groups of the adsorbed polymer with at least one crosslinking reagent;
   (iv) derivatizing further defined portions of the functional groups of the crosslinked polymer with first residues comprising a pyridyl ring ($-C_5H_4N$), wherein the hydrogen atoms may be substituted, and with second residues comprising a carboxyl group ($-COOH$), and optionally with further residues.

14. A method of separating, or increasing the concentration and/or purity of a protein or peptide from a mixture containing the protein or peptide, comprising:
   (i) contacting the mixture which is dissolved or suspended in a first liquid, with the sorbent of claim 11 for a period of time sufficient to enable the protein or peptide in the mixture to become bound to the sorbent;
   (ii) optionally rinsing the sorbent bound with the protein or peptide with a second liquid;
   (iii) contacting the sorbent bound with the protein or peptide with a third liquid for a period of time sufficient to enable the protein or peptide to become released from the sorbent; and
   (iv) optionally washing and/or regenerating the sorbent with a fourth and/or a fifth liquid.

15. The method of claim 14, wherein the pH of the third liquid is close to the isoelectric point (pi) of the protein or peptide to be released from the sorbent.

16. The method of claim 14, wherein the pH of the first liquid is in the range of from 4.0 to 6.0, and the pH of the third liquid is in the range of from 6.5 to 8.5.

17. The method of claim 14, wherein the protein or peptide exhibits an isoelectric point (pi) of from 4.5 to 8.5, and exhibits a molecular weight of from 100 to 500,000 Daltons (Da).

18. The method of claim 14, wherein the protein or peptide is selected from a natural antibody and fragments thereof, an oligomeric associate derived from a natural antibody, a genetically engineered antibody, and an antibody- or antibody fragment-containing fusion protein.

19. The method of claim 14, wherein the natural antibody is an immunoglobulin G.

20. The method of claim 14, wherein the mixture containing the protein or peptide is selected from human blood, an intermediate derived from human blood, a finished product derived from human blood, blood plasma and any proteinaceous precipitate obtained by fractionation of blood plasma.

* * * * *

UNITED STATES PATENT AND TRADEMARK OFFICE
CERTIFICATE OF CORRECTION

PATENT NO. : 9,061,267 B2
APPLICATION NO. : 13/515653
DATED : June 23, 2015
INVENTOR(S) : Klaus Gottschall et al.

It is certified that error appears in the above-identified patent and that said Letters Patent is hereby corrected as shown below:

In the Claims

Column 56, Line 33: "residues resent" should be --residues present--.

Column 56, Line 37: "based the tote" should be --based the total--.

Column 56, Line 41: "solid material" should be --solid support material--.

Column 56, Line 42: "sultanate" should be --sulfonate--.

Column 56, Line 50: "sultanate" should be --sulfonate--.

Signed and Sealed this
Eighteenth Day of August, 2015

Michelle K. Lee
*Director of the United States Patent and Trademark Office*